United States Patent
Masuda et al.

(10) Patent No.: US 12,319,751 B2
(45) Date of Patent: Jun. 3, 2025

(54) ANTI-IGE ANTIBODY SPECIFICALLY BINDING TO MEMBRANE-BOUND IGE ANTIBODY OF IGE ANTIBODY-PRODUCING B CELLS AND METHOD FOR DIAGNOSING AND TREATING ALLERGIC SYMPTOMS USING THE SAME

(71) Applicants: RIKEN, Saitama (JP); ANIMAL ALLERGY CLINICAL LABORATORIES INC., Sagamihara (JP)

(72) Inventors: Kenichi Masuda, Saitama (JP); Takashi Saito, Saitama (JP)

(73) Assignees: RIKEN, Saitama (JP); ANIMAL ALLERGY CLINICAL LABORATORIES INC., Kanagawa (JP)

( * ) Notice: Subject to any disclaimer, the term of this patent is extended or adjusted under 35 U.S.C. 154(b) by 1039 days.

(21) Appl. No.: 17/278,164

(22) PCT Filed: Sep. 20, 2019

(86) PCT No.: PCT/JP2019/036864
§ 371 (c)(1),
(2) Date: Mar. 19, 2021

(87) PCT Pub. No.: WO2020/059832
PCT Pub. Date: Mar. 26, 2020

(65) Prior Publication Data
US 2021/0355237 A1 Nov. 18, 2021

(30) Foreign Application Priority Data
Sep. 21, 2018 (JP) .................................. 2018-176768

(51) Int. Cl.
*C07K 16/42* (2006.01)
*G01N 33/68* (2006.01)

(52) U.S. Cl.
CPC ..... *C07K 16/4291* (2013.01); *G01N 33/6854* (2013.01); *C07K 2317/24* (2013.01); *G01N 2800/24* (2013.01); *G01N 2800/50* (2013.01)

(58) Field of Classification Search
None
See application file for complete search history.

(56) References Cited

U.S. PATENT DOCUMENTS

| | | |
|---|---|---|
| 5,478,926 A | 12/1995 | Nishimura et al. |
| 2017/0121425 A1 | 5/2017 | Chen et al. |
| 2017/0158738 A1 | 6/2017 | Masuda et al. |

FOREIGN PATENT DOCUMENTS

| | | | |
|---|---|---|---|
| JP | 04-126094 A | | 4/1992 |
| JP | 09169795 A | * | 6/1997 |
| JP | 2017-518320 A | | 7/2017 |
| WO | WO-00/50460 A1 | | 8/2000 |
| WO | WO-2015/190555 A1 | | 12/2015 |

OTHER PUBLICATIONS

Mariuzza, R.A. et al. 'The Structural Basis of Antigen-Antibody Recognition1 Annu. Rev. Biophys. Biphys. Chem. 16:139-159, 1987.*
Rudikoff et al. 'Single amino acid substitutions altering antigen-binding specificity.' PNAS 79:1979-1983, 1982.*
Rader et al. 'A phage display approach for rapid antibody humanization designed combinatorial V gene libraries.'PNAS 95:8910-8915, 1998.*
Maccallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Goel et al. Plasticity within the Antigen-Combining Site May Manifest as Molecular Mimicry in the Humoral Immune Response. 1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*
Poosarla et al. 'Computational De Novo Design of Antibodies Binding to a Peptide With High Affinity.' Biotech. Bioeng. 114(6): 1331-1342, 2017.*
Harris et al., "A randomized trial of quilizumab in adults with refractory chronic spontaneous urticaria," J. Allergy Clin. Immunol., Jul. 19, 2016, 138(6):1730-1732.
Harris et al., "A randomized trial of the efficacy and safety of quilizumab in adults with inadequately controlled allergic asthma," Respiratory Research, Mar. 18, 2016, 17:29, 11 pages.
International Search Report dated Dec. 3, 2019 in PCT/JP2019/036864.
Okayama et al., "Establishment of a quantitative ELISA for the measurements of allergen-specific IgE in dogs using anti-IgE antibody cross-reactive to mouse and dog IgE," Veterinary Immunology and Immunopathology, 2011 (online Sep. 21, 2010), 139(2-4):99-106.
Zheng et al., "Fine epitope mapping of humanized anti-IgE monoclonal antibody omalizumab," Biochemical and Biophysical Research Communications, 2008, 375:619-622.

(Continued)

*Primary Examiner* — Nora M Rooney
(74) *Attorney, Agent, or Firm* — Foley & Lardner LLP

(57) ABSTRACT

The present invention provides an antibody specific to IgE antibody-producing B cells or an antibody binding fragment thereof. More specifically, the present invention provides an isolated monoclonal antibody or an antigen binding fragment thereof that binds to a peptide having a sequence consisting of an amino acid sequence set forth in SEQ ID NO: 1 or 18, and
(1) binds to IgE antibody on a B cell surface and/or
(2) binds to IgE antibody heated at 56° C.

15 Claims, 20 Drawing Sheets

Specification includes a Sequence Listing.

(56) References Cited

OTHER PUBLICATIONS

Baniyash et al., "Inhibition of IgE binding to mast cells and basophils by monoclonal antibodies to murine IgE," Eur. J. Immunol., Sep. 1, 1984, 14(9):799-807.
Chretien et al., "A monoclonal anti-IgE antibody against an epitope (amino acids 367-376) in the CH3 domain inhibits IgE binding to the low affinity IgE receptor (CD23)," The Journal of Immunology, Nov. 1, 1988, 141(9):3128-3134.
Supplementary European Search Report dated May 27, 2022 in EP 19863519.5.
Database Genbank, "*Homo sapiens* Ig heavy chain epsilon-1 (V-D-J region) (IGHE) Gene, complete cds," Jul. 28, 2016, AH005278.2.
Dorrington et al., "Structure-Function Relationships in Human Immunoglobulin E," Immunological Rev., 1978, 41:3-25.
Office Action dated Feb. 6, 2024 in JP 2020-549095.

\* cited by examiner

6C12 is an anti-IgE antibody reacting to human and animal IgE except mouse IgE.

FIG. 3
6C12 detects IgE changed in conformation by heating. Clinical specimen contains IgE detected after denatured by heating. That is considered as pathogenic IgE.
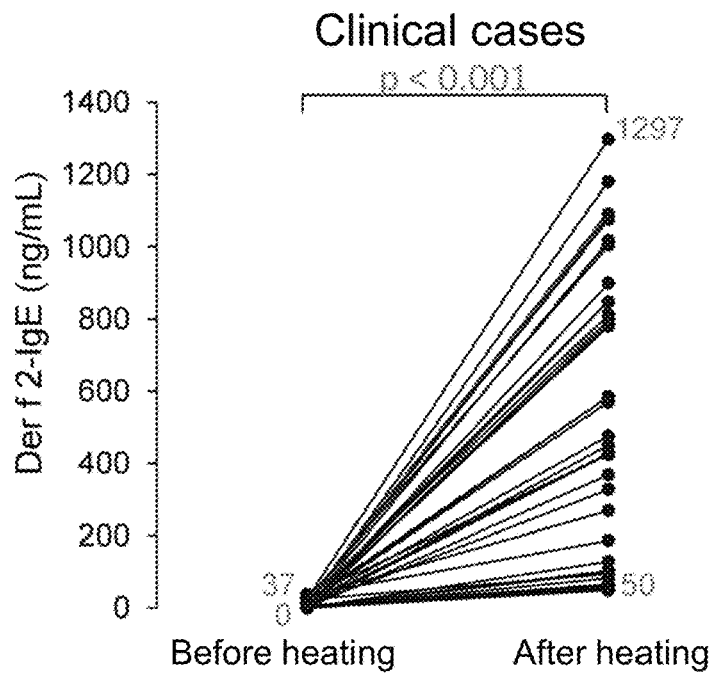
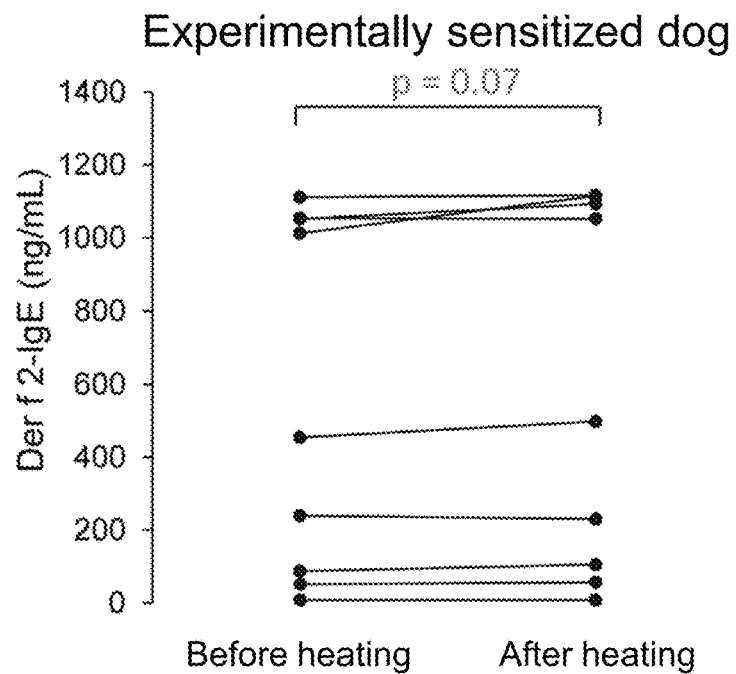

IgE in blood is changed by heating to non-pathogenical IgE

IgE recognized by 6C12: non-pathogenic

6C12 detects IgE changed in conformation by heating. Pathogenic IgE can be calculated from IgE values before and after heating.

Pathogenic IgE value =
IgE value after heating - IgE value before heating

6C12 binds to IgE on B cell surface

IgE producing B cells in canine peripheral blood mononuclear cells stimulated with ConA and cultured for three days 6C12 does not bind to IgE on mast cells Canine antibody drug of 6C12

|  | Dog 1 | Dog 2 | Dog 3 | Average |
|---|---|---|---|---|
| Canine recombinant chimeric antibody of 6C12 10 µg/ml | 48 | 61 | 90 | 66.3 |
| Canine recombinant antibody for control 10 µg/ml | 0 | 0 | 0 | 0 |

FIG. 15
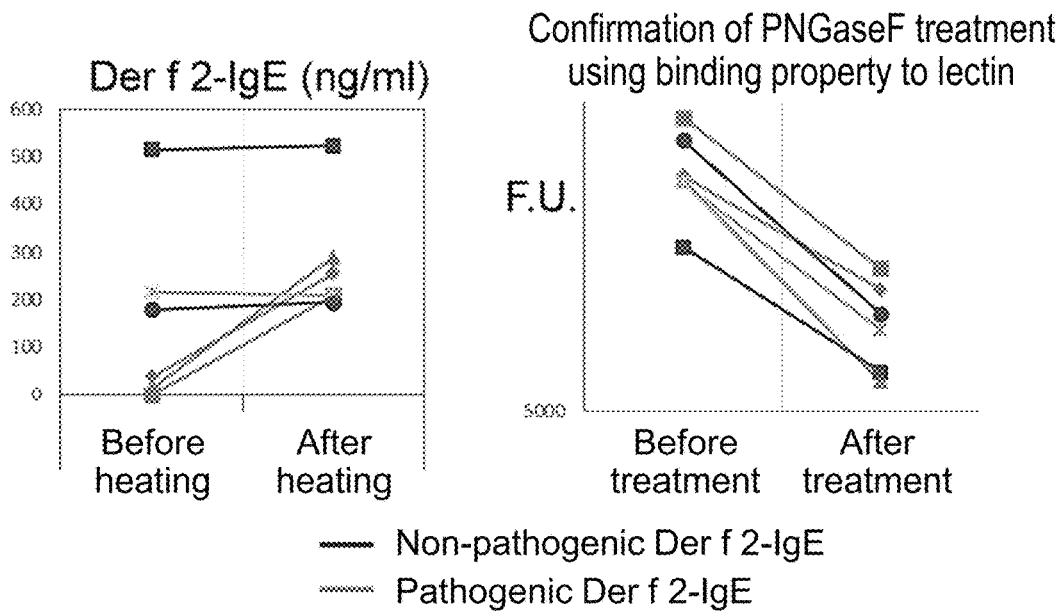
FIG. 16
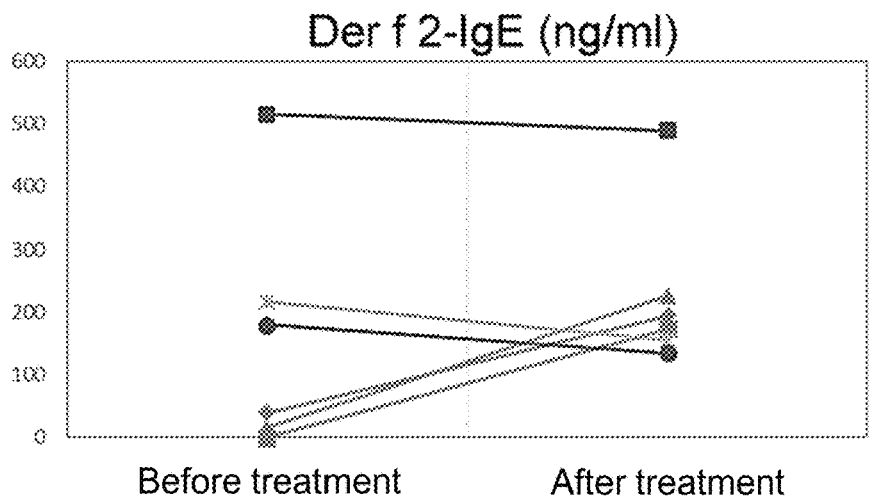
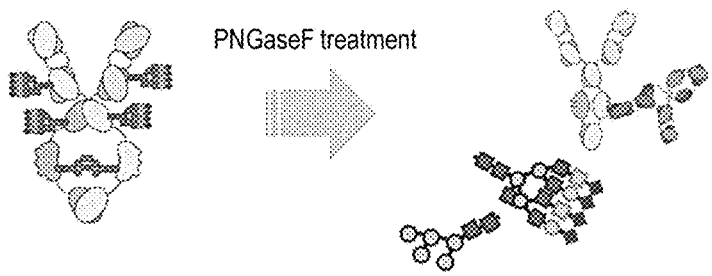

FIG. 17
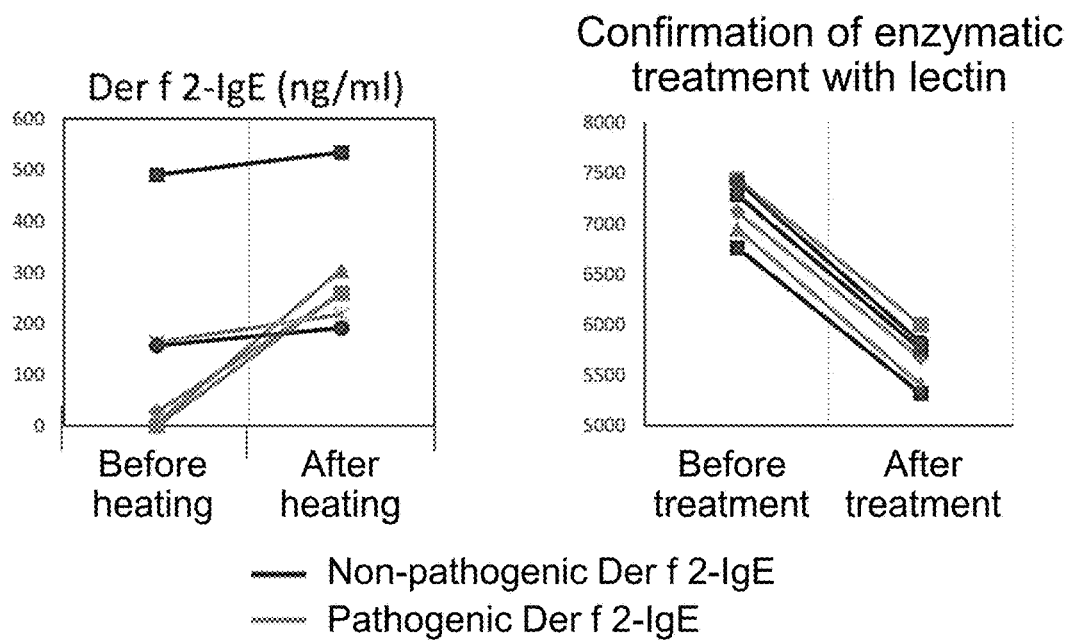
— Non-pathogenic Der f 2-IgE
— Pathogenic Der f 2-IgE
FIG. 18
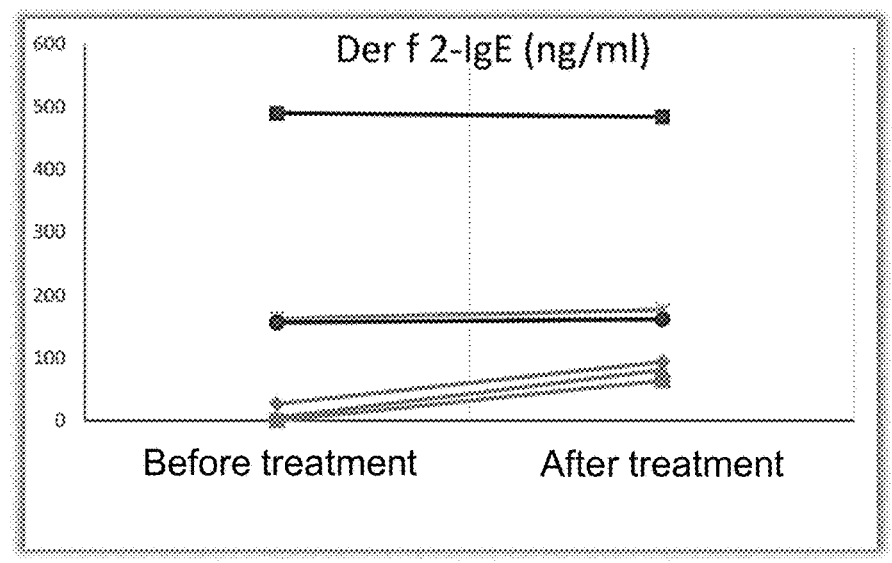
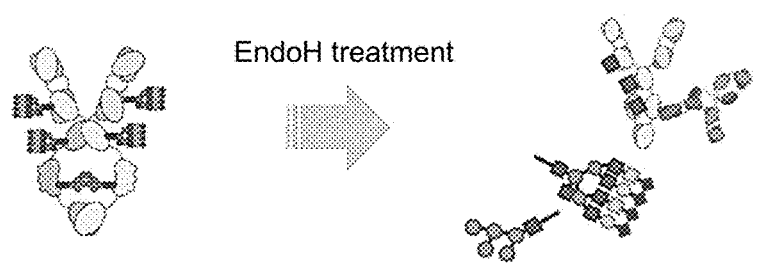
EndoH treatment

FIG. 20
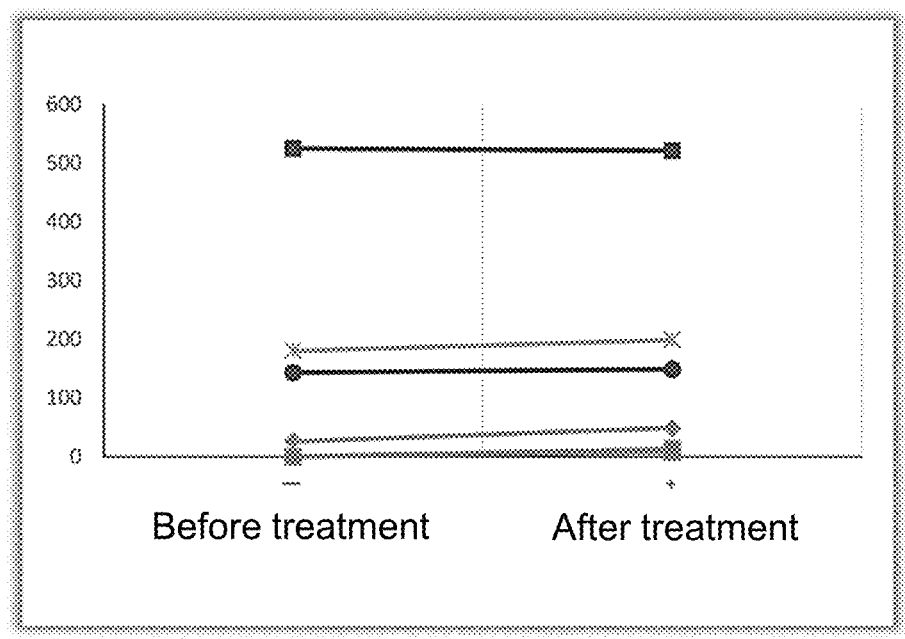
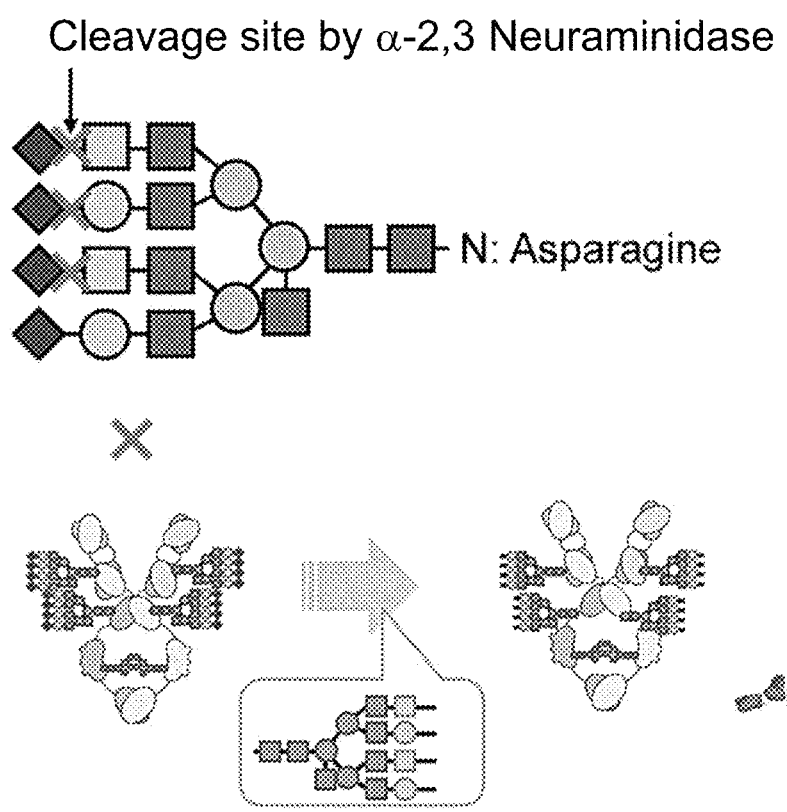
Cleavage site by α-2,3 Neuraminidase
N: Asparagine

FIG. 21

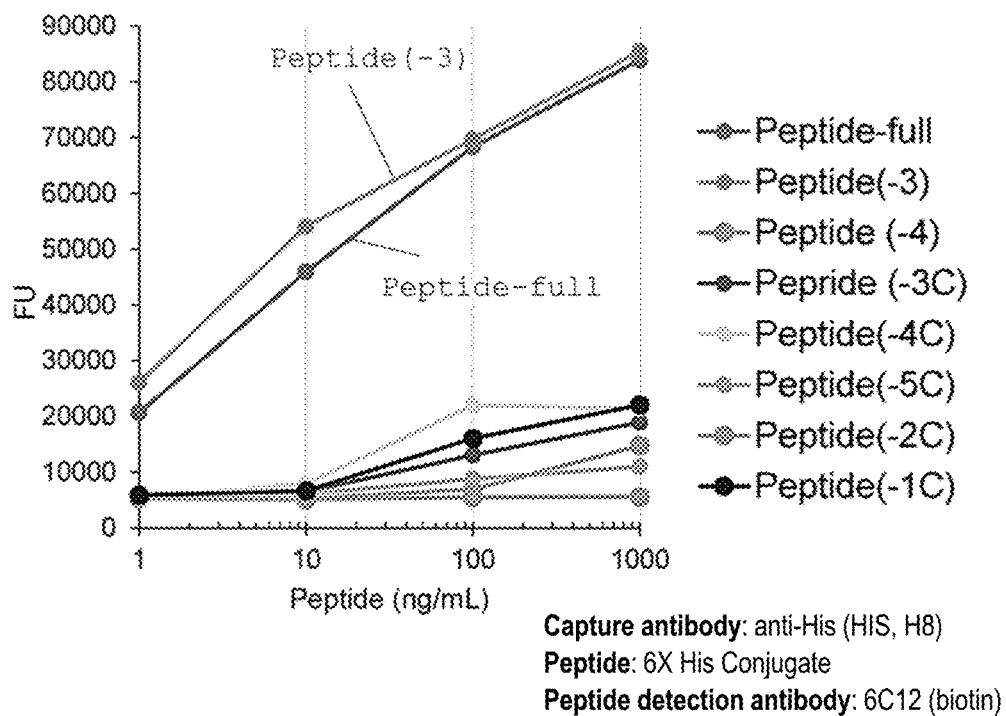

Capture antibody: anti-His (HIS, H8)
Peptide: 6X His Conjugate
Peptide detection antibody: 6C12 (biotin)

```
Peptide-full:   HHHHHHGGSGGSNTNDWIEGETYYC
Peptide(-3):          HHHHHHGGSGGSDWIEGETYYC
Peptide(-4):           HHHHHHGGSGGSWIEGETYYC
Peptide(-3C):   HHHHHHGGSGGSNTNDWIEGET
Peptide(-4C):   HHHHHHGGSGGSNTNDWIEGE
Peptide(-5C):   HHHHHHGGSGGSNTNDWIEG
Peptide(-2C):   HHHHHHGGSGGSNTNDWIEGETY
Peptide(-1C):   HHHHHHGGSGGSNTNDWIEGETYY
```

FIG. 22
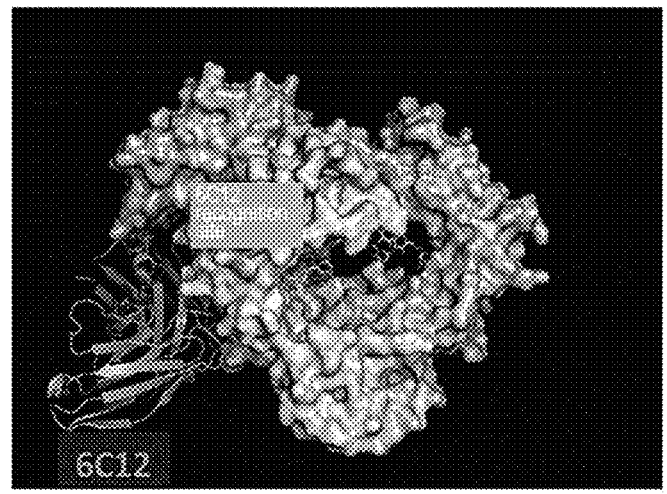
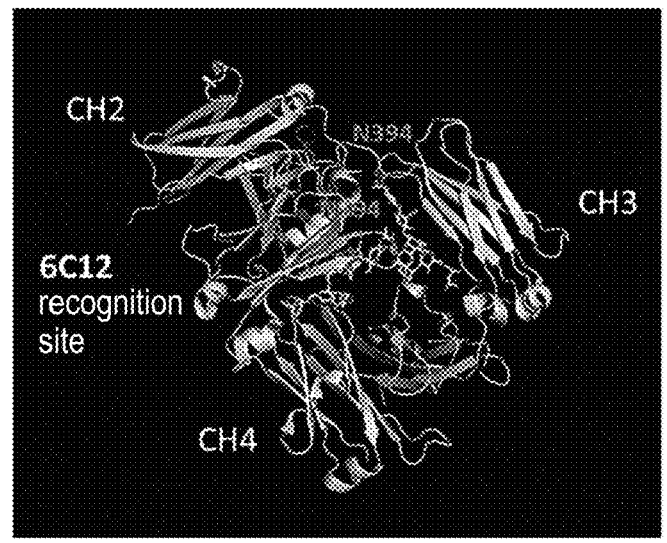
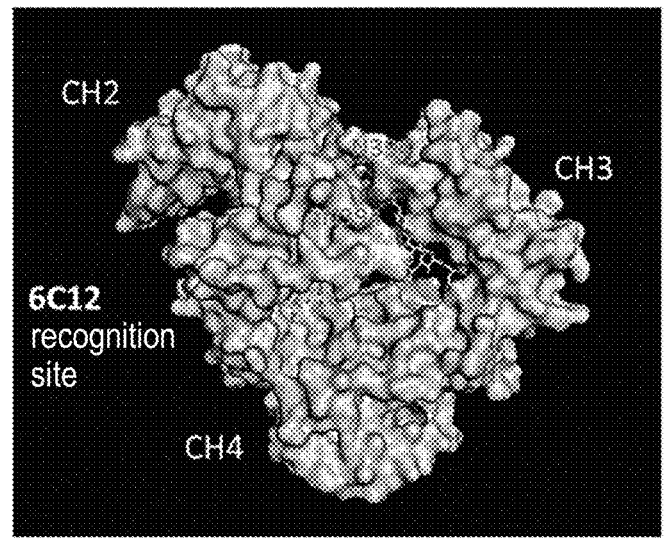

FIG. 23

Amino acid sequence number of IgE heavy-chain constant region (described based on the sequence number in the canine)

Glycosylation site corresponding to N394 in Human IgE heavy-chain sequence

FIG. 25

Homology of peripheral region of peptide sequence used as immunogen

Positions in amino acid sequence of IgE heavy-chain constant region (described based on positions in the canine sequence)

Bold letters represent animal species and human on which experiment data were obtained.

| | | 280     290     300 |
|---|---|---|
| Human | | LPVGTRDWIEGETYQCRVTHPHLP |
| Monkey | | LPVVTQDWIEGETYQCRVTHPHLP |
| Dog | | LPVNTNDWIEGETYYCRVTHPHLP |
| Cat\* | | LPVDATDWVEGETYQCKVTHPDLP |
| Horse | | LPVDTTDWIEGETYKCTVSHPDLP |
| Cow | | LPVDVTDWVEGETYYCKVSHSDLP |
| Pig | | LPVNVSDWIEGETYYCNVTHPDLP |
| Rat | | LPVDAKDWIEGEGYQCRVDHPHFP |
| Mouse | | LPVVAKDWIEGYGYQCIVDHPDFP |

Peptide sequence used for immunization

ANTI-IGE ANTIBODY SPECIFICALLY BINDING TO MEMBRANE-BOUND IGE ANTIBODY OF IGE ANTIBODY-PRODUCING B CELLS AND METHOD FOR DIAGNOSING AND TREATING ALLERGIC SYMPTOMS USING THE SAME

CROSS-REFERENCE TO RELATED APPLICATIONS

This application is the U.S. National Stage of PCT/JP2019/036864, filed Sep. 20, 2019, which claims priority to JP 2018-176768, filed Sep. 21, 2018.

The instant application contains a Sequence Listing which has been submitted in ASCII format via EFS-WEB and is hereby incorporated by reference in its entirety. Said ASCII copy, created on Mar. 17, 2021, is named sequence.txt and is 8,105 bytes.

TECHNICAL FIELD

The present invention relates to an anti-IgE antibody that specifically binds to membrane-bound IgE antibody of IgE antibody-producing B cells and a method for diagnosing and treating an allergic symptom using the same. More specifically, the present invention provides an anti-IgE antibody that binds to membrane-bound IgE antibody of IgE antibody-producing B cells and does not substantially bind to IgE antibody bound to mast cells. The present invention provides an anti-IgE antibody that does not substantially bind to non-heated IgE antibody and binds to heated IgE antibody.

BACKGROUND ART

It is known that mast cells are involved in an allergic symptom. For example, in allergies such as hay fever and bronchial asthma, mast cells react with an allergen such as a pollen and a tick-derived protein, and release a physiologically active substance such as histamine, which causes inflammation. On the cell surface of the mast cells, an IgE antibody receptor (FcεRI) is expressed, which has high affinity to IgE antibody. When the IgE antibody binds to FcεRI, conformational change occurs. In this way, the IgE antibody is prepared for contact with an allergen. When the IgE antibody binds to an allergen and at least two IgE antibody molecules are crosslinked, FcεRIs are assembled and FcεRI signal is transmitted to cells, with the result that mast cells are degranulated to release, e.g., histamine.

As a therapeutic strategy for allergic symptoms, an attempt to suppress the function of IgE antibody has been made. For example, in Non Patent Literature 1, an anti-IgE antibody, omalizumab, is used, which is an antibody that binds to IgE antibody in the blood and serves as an antibody drug suppressing allergic symptoms by decreasing the level of IgE antibody in the blood (Non Patent Literature 1). However, since omalizumab does not react with IgE antibody-producing cells, omalizumab conceivably cannot suppress production of IgE antibody (Non Patent Literature 1). Also, quilizumab is an antibody that binds to membrane-bound IgE antibody of IgE antibody-producing cells, and thereby, can exclude IgE antibody-producing cells. Thus, quilizumab serves as an antibody drug suppressing an allergic symptom (Non Patent Literatures 2 and 3). However, quilizumab reacts also to IgE antibody in the blood, and thereby, the antibody is consumed in the blood in patients having a high blood level of IgE antibody. Because of this, a low suppressive effect thereof on an allergic symptom is concerned (Non Patent Literatures 2 and 3).

CITATION LIST

Patent Literature

Patent Literature 1: WO2015/190555

Non Patent Literatures

Non Patent Literature 1: Zheng, L. et al., 2008, Biochem. Biophys. Res. Commun., 375:619-622
Non Patent Literature 2: Harris, J. M. et al., 2016, J. Allergy Clin. Immunol., 138:1730-1732
Non Patent Literature 3: Harris, J. M. et al., 2016, Respir. Res., 17:29

SUMMARY OF INVENTION

The present invention provides an anti-IgE antibody that specifically binds to membrane-bound IgE antibody of IgE antibody-producing B cells, and a method for diagnosing and treating an allergic symptom by using said antibody.

The present inventors have found that a monoclonal antibody, which is obtained by using a peptide of 13 amino-acid length having a sequence consisting of the amino acid sequence set forth in SEQ ID NO: 1 as an immunogen, binds to IgE antibody-producing B cells and IgE antibody changed in conformation by heating (hereinafter, sometimes referred to as "heated IgE antibody"). The present inventors also have found that substantial binding is made neither to IgE antibody not heated (having no conformational change by heating) in clinical specimens (hereinafter, sometimes referred to as a "non-heated IgE antibody") nor IgE antibody on the surface of mast cells. The present invention is based on these findings.

According to the present invention, the following embodiments are provided.

[1] An isolated monoclonal antibody or an antigen binding fragment thereof that binds to a peptide having a sequence consisting of the amino acid sequence set forth in SEQ ID NO: 1 or 18, and
(1) binds to IgE antibody on a B-cell surface, and/or
(2) binds to IgE antibody heated at 56° C.
[2] The antibody or an antigen binding fragment thereof according to [1], wherein the antibody or an antigen binding fragment thereof binds to a peptide having a sequence consisting of the amino acid sequence set forth in SEQ ID NO: 1 or 18, and
(1) binds to IgE antibody on a B-cell surface.
[3] The antibody or an antigen binding fragment thereof according to above [1], wherein the antibody or an antigen binding fragment thereof binds to a peptide having a sequence consisting of the amino acid sequence set forth in SEQ ID NO: 1 or 18, and
(2) binds to a free IgE antibody heated at 56° C.
[4] The antibody according to above [1], wherein the antibody or an antigen binding fragment thereof
(1) binds to IgE antibody on a B-cell surface, and
(2) binds to a free IgE antibody heated at 56° C.
[5] The antibody or an antigen binding fragment thereof according to above [2] or [4], wherein the antibody or an antigen binding fragment thereof has stronger affinity to IgE antibody on the B-cell surface than IgE antibody on a mast-cell surface.

[6] The antibody or an antigen binding fragment thereof according to above [3] or [4], wherein the antibody or an antigen binding fragment thereof has stronger affinity to a free IgE antibody heated at 56° C. than the free IgE antibody before heating.

[7] The antibody or an antigen binding fragment thereof according to any one of above [1] to [7], wherein the antibody or an antigen binding fragment thereof has
a heavy chain variable region comprising heavy chain CDR1 having the amino acid sequence set forth in SEQ ID NO: 2, heavy chain CDR2 having the amino acid sequence set forth in SEQ ID NO: 3 and heavy chain CDR3 having the amino acid sequence set forth in SEQ ID NO: 4, and
a light chain variable region comprising light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

[8] The antibody or an antigen binding fragment thereof according to above [7], wherein the antibody or an antigen binding fragment thereof has a heavy chain variable region having the amino acid sequence set forth in SEQ ID NO: 8 and a light chain variable region having the amino acid sequence set forth in SEQ ID NO: 9.

[9] A caninized antibody of the antibody according to any one of above [1] to [8], or an antigen binding fragment thereof.

[10] A felinized antibody of the antibody according to any one of above [1] to [8], or an antigen binding fragment thereof.

[11] A pharmaceutical composition comprising the antibody or an antigen binding fragment thereof according to any one of above [2], [4], [5], [7] and [8].

[12] A composition comprising the antibody or an antigen binding fragment thereof according to any one of above [3], [4], [6], [7] and [8], for use in detection of free IgE antibody heated.

[13] A method for examining an allergic symptom or a risk of developing the symptom in a mammal, comprising
heating a biological sample obtained from a mammal to obtain a biological sample containing a free IgE antibody that reacts with the antibody according to any one of above [3], [4], [6], [7] and [8] and
bringing the heated biological sample into contact with the antibody or an antigen binding fragment thereof according to any one of above [3], [4], [6], [7] and [8].

[14] The method according to above [13], further comprising
bringing the biological sample of a mammal before heating into contact with the antibody or an antigen binding fragment thereof according to any one of above [3], [4], [6], [7] and [8].

[15] The method according to above [14], further comprising
comparing reactivity of the antibody or an antigen binding fragment thereof according to any one of above [3], [4], [6], [7] and [8] to a biological sample obtained from a mammal before and after heating the biological sample.

Accordingly, the antibody that does not bind to a free IgE antibody in the blood, and IgE antibody bound to mast cells, and binds to membrane-bound IgE antibody of IgE antibody-producing B cells (plasma cells) can be beneficial for treating allergic diseases or conditions.

BRIEF DESCRIPTION OF DRAWINGS

FIG. 3 shows that the anti-IgE antibody of the present invention binds to IgE antibody changed in conformation by heating the serum in clinical cases of allergy. FIG. 3 also shows that binding is made to any one of IgE antibodies before and after heating of the serum in experimentally sensitized examples.

FIG. 15 shows that the binding property of 6C12 antibody to pathogenic IgE antibody varies depending on heating and the results of deglycosylation of pathogenic IgE antibody with PNGaseF.

FIG. 16 shows that 6C12 antibody can bind to pathogenic IgE antibody after deglycosylation with PNGaseF.

FIG. 17 shows that the binding property of 6C12 antibody to pathogenic IgE antibody varies depending on heating and shows the results of deglycosylation of pathogenic IgE antibody with EndoH.

FIG. 18 shows that 6C12 antibody can bind to pathogenic IgE antibody after deglycosylation with EndoH.

FIG. 20 shows that 6C12 antibody cannot bind to pathogenic IgE antibody after deglycosylation with α-2,3 neuraminidase.

FIG. 21 shows binding properties of 6C12 antibody and various peptides.

FIG. 22 shows the simulation of binding state between 6C12 antibody and IgE antibody.

Figure 23:
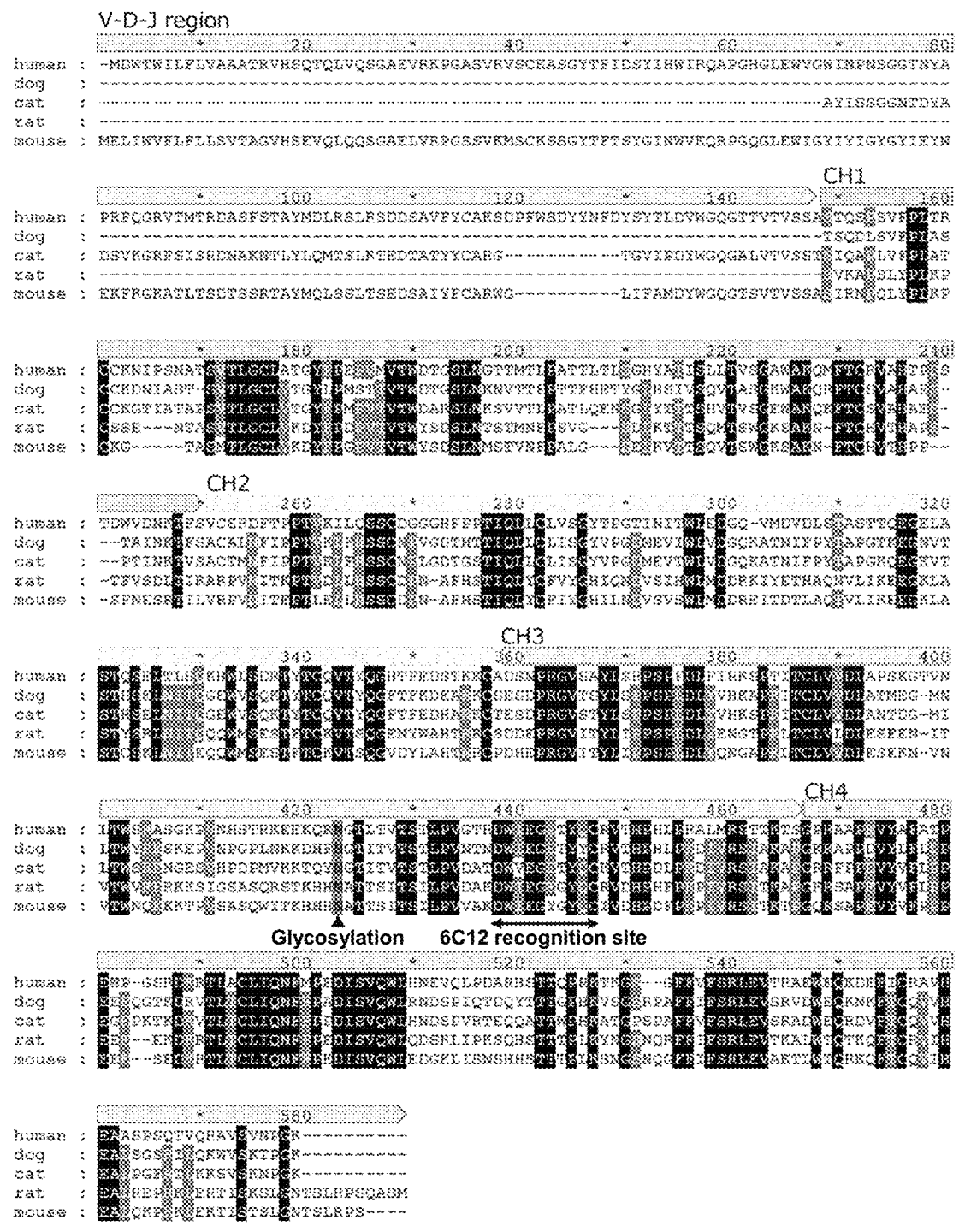

FIG. 23 shows alignment data of heavy chain amino acid sequences of IgE antibodies of a human, dog, cat, rat and mouse in the order from the top.

FIG. 25 shows the homology of the peripheral region of an immunogen peptide sequence across various animal species, including human, monkey, dog, cat, horse, cow, pig, rat, and mouse.

DESCRIPTION OF EMBODIMENTS

Figure 1:
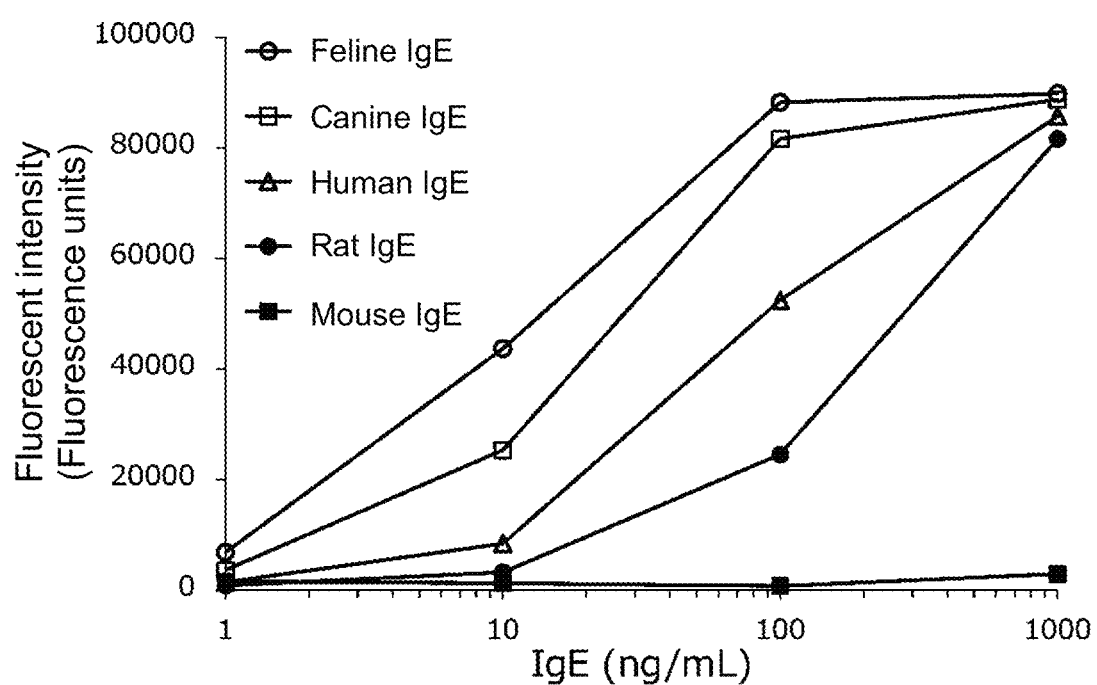
FIG. 1 shows that the anti-IgE antibody of the present invention binds to IgE antibodies of various mammals.

In the specification, the "subject" refers to a mammal such as a pet animal including a dog and a cat; a farm animal including a horse, a cow, a sheep, a goat and a pig; a rodent including a rat and a hamster; and a primate including a monkey, an orangutan, a gorilla, a chimpanzee, a bonobo and a human.

In the specification, the "antibody" refers to an immunoglobulin, which is a protein having a conformation having two heavy chains (H chains) and two light chains (L chains) associated and stabilized by a pair of disulfide bonds. The heavy chain consists of a heavy chain variable region (VH), heavy chain constant regions (CH1, CH2, and CH3) and a hinge region located between CH1 and CH2; whereas the light chain consists of a light chain variable region (VL) and a light chain constant region (CL). Of them, a variable region fragment (Fv) consisting of VH and VL is directly involved in binding to antigens and is a region adding diversity to the antibody. The antigen-binding region consisting of VL, CL, VH and CH1 is called Fab region; whereas the region consisting of a hinge region, CH2 and CH3 is called Fc region. The heavy chain and light chain are produced as precursors having a signal sequence in a cell, the signal sequence is cleaved and removed and an antibody can be produced from an antibody-producing cell.

In the variable region, the region directly in contact with an antigen is hypervariable and called a complementarity-determining region (CDR). The relatively less mutated region except CDR is called a framework region (FR). The variable regions of a light chain and a heavy chain each have three CDRs and are called heavy chain CDR1 to 3 and light chain CDR1 to 3, respectively in the order from the N terminal side.

In the specification, the "treatment" refers to therapy or prophylaxis. Accordingly, a "pharmaceutical composition for use in treating cancer" in the specification refers to pharmaceutical composition for use in therapy or prophylaxis of cancer, including an anticancer agent, as an example.

The antibody that binds to the IgE antibody of the present invention may be a monoclonal antibody or a polyclonal antibody. Also, the antibody that binds to the IgE antibody of the present invention may be any one of isotypes of IgG, IgM, IgA, IgD and IgE. The monoclonal antibody may substantially consist of a single type of antibody such as a non-recombinant antibody and recombinant antibody produced from a single cell strain. The monoclonal antibody may be produced by immunizing a non-human animal such as a mouse, a rat, a hamster, a guinea pig, a rabbit and a chicken, or may be a recombinant antibody; or a chimeric antibody, a humanized antibody, a fully humanized antibody, a caninized antibody, a fully canine antibody, a felinized antibody, a fully feline antibody, and the like. The chimeric antibody refers to an antibody obtained by connecting antibody fragments derived from different species. The antibody that binds to the IgE antibody of the present invention is preferably an antibody that does not substantially bind to isotypes of antibodies except IgE antibody. The antibody that binds to the IgE antibody of the present invention may be an antibody having an antibody-dependent cellular cytotoxicity (ADCC activity) and/or a complement-dependent cytotoxicity (CDC activity). Thereby, the antibody attacks IgE antibody-producing B cells and expectedly has a removal effect of them from a living body. An isotype such as IgG1 and IgG2a may have a strong ADCC activity. In the specification, an "antibody that binds to IgE antibody" is sometimes referred to as an "anti-IgE antibody". The antibody that binds to the IgE antibody of the present invention or an IgE antibody-binding fragment thereof may be in a form of a conjugate with a cytotoxic agent, that is, a drug antibody conjugate (ADC). Thereby, the antibody or a fragment thereof attacks IgE antibody-producing B cells and expectedly has a removal effect of them from a living body. Also, in the present invention, the "IgE antibody" refers to a free IgE antibody unless otherwise specified. The "free IgE antibody" refers to IgE antibody not bound to membrane unlike membrane-bound IgE antibody. In the specification, the "pathogenic IgE antibody" refers to IgE antibody capable of binding to mast cells.

The "humanized antibody" refers to an antibody obtained by substituting the amino acid sequence characteristic to the non-human antibody for the corresponding sequence of a human antibody; and is, for example, an antibody having heavy chain CDR1 to 3 and light chain CDR1 to 3 of an antibody, which is produced by immunizing a mouse or rat, and the other regions (including four framework regions (FR) of the heavy chains and light chains) all derived from a human antibody. Such an antibody is sometimes called as a CDR-grafted antibody. The term "humanized antibody" sometimes includes a human chimeric antibody.

The "human chimeric antibody" is a non-human antibody obtained by substituting the constant region of the non-human antibody with the constant region of a human antibody. In a human chimeric antibody, in order to enhance ADCC activity, for example, IgG1 can be employed as the subtype of a human antibody for use in the constant region.

The "caninized antibody" refers to an antibody obtained by substituting the amino acid sequence characteristic to a non-canine antibody for the corresponding sequence of a canine antibody; and is, for example, an antibody, having heavy chain CDR1 to 3 and light chain CDR1 to 3 of an antibody, which is produced by immunizing a mouse or rat, and the other regions (including four framework regions (FR) of the heavy chains and light chains) all derived from a canine antibody. Such an antibody is sometimes called as a CDR-grafted antibody. The term "caninized antibody" sometimes includes a canine chimeric antibody.

The "canine chimeric antibody" is a non-canine antibody obtained by substituting the constant region of the non-canine antibody with the constant region of a canine antibody. In a canine chimeric antibody, in order to enhance ADCC activity, for example, IgGb can be employed as the subtype of a canine antibody for use in the constant region; however, the subtype is not limited to IgGb.

The "felinized antibody" refers to an antibody obtained by substituting the amino acid sequence characteristic to a non-feline antibody for the corresponding sequence of a feline antibody; and is, for example, an antibody, having heavy chain CDR1 to 3 and light chain CDR1 to 3 of an antibody, which is produced by immunizing a mouse or rat, and the other regions (including four framework regions (FR) of the heavy chains and light chains) all derived from a feline antibody. Such an antibody is sometimes called as a CDR-grafted antibody. The term "feline antibody" sometimes includes a feline chimeric antibody.

The "feline chimeric antibody" is a non-feline antibody obtained by substituting the constant region of the non-feline antibody with the constant region of a feline antibody.

The mammalianized antibody refers to an antibody obtained by substituting the amino acid sequence characteristic to an antibody of a mammal species with the corresponding sequence characteristic to that of another mammal species; and is, for example, an antibody having heavy chain CDR1 to 3 and light chain CDR1 to 3 of an antibody, which is produced by immunizing a mouse or rat, and all the other region including four framework regions (FR) of the heavy chains and light chains are derived from the mammal species. Such an antibody is sometimes called as a CDR-grafted antibody. The term "mammalianized antibody" sometimes includes a mammalian chimeric antibody.

The "mammalian chimeric antibody" is, in a mammalian species, an antibody obtained by substituting the constant region of an antibody of a species except a certain mammalian species by the constant region of the antibody of the certain mammalian species. In a mammalian chimeric antibody, in order to enhance ADCC activity, for example, the subtype of a mammalian antibody for use in the constant region can be IgG1, or IgGb in a dog.

A primatized antibody and a primate chimeric antibody are the same as defined above.

In the specification, the "antigen binding fragment" is an antibody fragment maintaining an ability to bind to IgE antibody. Examples thereof include, but are not limited to, Fab consisting of VL, VH, CL and CH1 regions; F(ab')2 having 2 Fabs linked via a disulfide bond at the hinge region; Fv consisting of VL and VH; a single chain antibody (scFv) having VL and VH linked via an artificial polypeptide linker; and a bispecific antibody such as a diabody, a scDb, tandem scFv and leucine zipper type antibodies.

In the specification, the "IgE antibody" is an immunoglobulin molecule formed of two heavy chains (E chain) and two light chains (κ chain or λ chain). In the specification, the "IgE antibody" is sometimes referred to as "IgE". The constant region of a heavy chain of IgE antibody is constituted of four domains, which are respectively called as Cal to 4 in the order from the side of the variable region. Domain Cε3 of IgE antibody is involved in binding to an IgE receptor (Fcε receptor). The Fcε receptor is expressed on the membrane surface of mast cells or IgE antibody-producing B cells. The Fcε receptor include FcεRI showing high affinity to IgE antibody and FcεRII showing low affinity to IgE antibody. FcεRI is expressed on the surface of mast cells; whereas FcεRII is expressed on the surface of B cells. When IgE antibody binds to FcεRI of mast cells and reacts with an allergen or a pathogen, a mediator such as histamine is released from the mast cells to cause an allergic reaction. In the specification, the IgE antibody that binds to mast cells is sometimes referred to as a "pathogenic IgE antibody" or a "pathogenic IgE". In the specification, heated IgE antibody and IgE antibody that does not bind to mast cells are sometimes referred to as "non-pathogenic IgE antibody" or "non-pathogenic IgE". The amino acid sequence of human IgE antibody can be an amino acid sequence registered in the GenBank at registration number: AH005278. The amino acid sequence of canine IgE antibody can be the amino acid sequence registered in the GenBank at registration number: L36872. The amino acid sequence of feline IgE antibody can be the amino acid sequence registered in the GenBank at registration number: AF162134. The amino acid sequence of rat IgE antibody can be the amino acid sequence registered in the GenBank at registration number: K02901. The amino acid sequence of mouse IgE antibody can be the amino acid sequence registered in the GenBank at registration number: LC387253.

In the specification, the "IgE antibody on the surface of B cell membrane" refers to B cell-binding IgE antibody. IgE antibody can bind to the surface of B cells via Fcε receptor. IgE antibody can be also expressed by a membrane-binding protein (for example, M1 protein in a mouse and M1' protein in a human) on the membrane surface of B cells producing IgE antibody. IgE antibody on the surface of B cell membrane can be a B cell receptor. B cells can be activated by stimulus (for example, stimulus to CD40 and stimulus by IL-4 or IL-13). CD40 can be activated with various means commonly known such as an anti-CD40 antibody. In place of an anti-CD40 antibody, a C4b-binding protein (C4BP) can also be used to stimulate CD40 on B cells. Further, stimulation of B cells by CD40 activates a TRAF (TNF-receptor associated factor) molecule within a B cell. The activation stimulus by LMP1, and a TNF receptor except CD40 (e.g., CD120a, CD120b), CD27, CD30, CD267, CD269, B cell activation factor (BAFF/Blys/CD257)-receptor (CD268), Toll-like receptor (TLR)) provides the same effect as that given by that to CD40. Alternatively, induction can be made by allowing cytokine (e.g., TNF and APRIL/CD256) of a TNF family to be in contact with B cells. Furthermore, in the human B cells, the B cells may be infected with Epstein-Barr virus (EBV), which induces tumorigenic transformation/growth of B cells. For inducing IgE production of B cells without using CD40 stimulus, a method for bringing IL-4, BAFF and an anti-IgM antibody simultaneously into contact with B cells, can be used. In place of IL-4, cytokine IL-13 analogous in its structure, can be used. As described, those skilled in the art can obtain stimulated B cells by appropriately using various methods commonly employed. The antibody of the present invention can bind to IgE on the surface of B cells thus stimulated.

In the specification, the "IgE antibody on the surface of mast cells" refers to IgE antibody bound to mast cells. IgE antibody can bind to mast cells via Fcε receptor.

According to the present invention, 6C12 shows binding property to a heat-denatured IgE antibody and IgE antibody on the surface of B cell membrane; and does not have reactivity to either IgE antibody before heat denaturation and IgE antibody on the surface of mast cells. From this, it is considered that IgE antibody on the surface of B cell membrane has the same conformation as in a heat denatured IgE antibody at least at a 6C12 epitope part, and has a different conformation from IgE antibody before heat denaturation and IgE antibody on the surface of mast cells.

In the specification, the "IgE antibody on the surface of mast cells" refers to IgE antibody bound to mast cells. IgE antibody can bind to mast cells via Fcε receptor.

In the specification, the "IgE antibody-producing B cells" refers to B cells (plasma cells) producing IgE antibody. B cells express IgM on the surface of cells after completion of V (D) J recombination of an immunoglobulin, and then, become mature B cells co-expressing IgD. Upon recognizing an antigen, mature B cells differentiate into plasma cells. In the final differentiation process of mature B cells into plasma cells, class switch recombination of a heavy chain constant region occurs, and a change in isotype from IgM to IgE occurs to produce B cells (plasma cells) producing IgE antibody. mRNA of mature Cα produced by B cells (plasma cells) producing IgE antibody may possibly encode a protein having a Cα region connected to a VDJ region.

In the specification, the "ADCC activity" refers to antibody-dependent cellular cytotoxicity. The ADCC activity refers to an activity to damage a target cell when the antibody of the present invention binds to a cell-surface antigen of the target cell, more specifically, by binding a Fcγ receptor-carrying cell (effector cell) to its Fc part via Fcγ receptor.

In the specification, the "CDC activity" refers to complement-dependent cytotoxic activity. The CDC activity refers to cytotoxic activity by a complement bound to an antibody.

In the specification, the "isolation" refers to taking out an antibody from the environment where the antibody is produced. Isolation can be a treatment for removing, for example, cells and cell debris present in the environment where the antibody is produced and other components in culture medium, including purification treatment for an antibody, for example, with an affinity column using a specific adsorbing material (e.g., protein A or protein G). Isolation can include, for example, solvent exchange.

According to the present invention, provided is an antibody that binds to a peptide having the amino acid sequence set forth in SEQ ID NO: 1 (NTNDWIEGETYYC), wherein the antibody binds to IgE antibody on the surface of B cell membrane. According to the present invention, provided is an antibody that binds to a peptide having the amino acid sequence set forth in SEQ ID NO: 11 (HHHHHHGGSGGSDWIEGETYYC). According to the present invention, provided is an antibody that binds to a peptide having the amino acid sequence set forth in SEQ ID NO: 11 (HHHHHHGGSGGSDWIEGETYYC), wherein the antibody binds to IgE antibody on the surface of B cell membrane. In some embodiments, the antibody that binds to a peptide having the amino acid sequence set forth in SEQ ID NO: 11 (HHHHHHGGSGGSDWIEGETYYC) binds to a peptide having the amino acid sequence set forth in at least one of SEQ ID NOs: 12 to 17 with a weaker affinity than the affinity to the peptide having the amino acid sequence set forth in SEQ ID NO: 11.

According to the present invention, provided is an antibody that binds to a peptide having the amino acid sequence set forth in SEQ ID NO: 18 (DWIEGETYYC). According to the present invention, provided is an antibody that binds to a peptide having the amino acid sequence set forth in SEQ ID NO: 18 (DWIEGETYYC), wherein the antibody binds to IgE antibody on the surface of B cell membrane. In some embodiments, the antibody that binds to a peptide having the amino acid sequence set forth in SEQ ID NO: 18 (DWIEGETYYC) binds to a peptide having the amino acid sequence set forth in at least one of SEQ ID NOS: 12 to 17 with a weaker affinity than the affinity to the peptide having the amino acid sequence set forth in SEQ ID NO: 18 (DWIEGETYYC).

The antibody of the present invention does not substantially react to IgE antibody on the surface of mast cell membrane. The phrase, does not substantially react, means, for example, that the reactivity of the antibody is 5 times or less, 4 times or less, 3 times or less, 2 times or less or 1.5 times or less as low as the reactivity of, e.g., a negative-control antibody (non-specific antibodies to IgE antibody such as an isotype control antibody that does not react to a predetermined antigen). The reactivity can be confirmed by a commonly known technique such as ELISA and flow cytometry.

According to the present invention, provided is an antibody that binds to a peptide having the amino acid sequence set forth in SEQ ID NO: 1 (NTNDWIEGETYYC), wherein the antibody binds to heated IgE antibody. According to the present invention, provided is an antibody that binds to a peptide having the amino acid sequence set forth in SEQ ID NO: 11 (HHHHHHGGSGGSDWIEGETYYC), wherein the antibody binds to heated IgE antibody. According to the present invention, provided is an antibody that binds to a peptide having the amino acid sequence set forth in SEQ ID NO: 18 (DWIEGETYYC), wherein the antibody binds to heated IgE antibody.

The antibody of the present invention according to an embodiment can bind to heated IgE antibody (for example, it may be a pathogenic IgE, an antibody having glycosylation at N394 in a human IgE). IgE antibody can be heated at, for example, 56° C. for one to several hours, 10 to 20 minutes or 15 minutes. The antibody of the present invention according to an embodiment does not substantially react to non-heated IgE antibody (for example, antibody allowed to stand still at 4° C. to 37° C.). The phrase "does not substantially react" means that the reactivity of the antibody is 5 times or less, 4 times or less, 3 times or less, 2 times or less or 1.5 times or less as low as the reactivity of, e.g., a negative-control antibody (antibodies non-specific to IgE antibody such as an isotype control antibody that does not react to a predetermined antigen). The reactivity can be confirmed by a commonly known technique such as ELISA and flow cytometry. The antibody of the present invention according to an embodiment has a dissociation constant ($K_D$ value) of $10^{-5}$ or less, $10^{-4}$ or less, $10^{-3}$ or less or $10^{-2}$ or less for non-heated IgE.

The antibody of the present invention according to an embodiment can have affinity to heated IgE antibody, which is 5 times or more, 6 times or more, 7 times or more, 8 times or more, 9 times or more, 10 times or more, 20 times or more, 30 times or more, 40 times or more, 50 times or more, 60 times or more, 70 times or more, 80 times or more, 90 times or more or 100 times or more as high as that to non-heated IgE antibody. The antibody of the present invention according to an embodiment can have a dissociation constant ($K_D$ value) for heated IgE antibody, which is $10^{-3}$, $10^{-4}$, $10^{-5}$, $10^{-6}$, $10^{-7}$, $10^{-8}$ or $10^{-9}$ as low as that for non-heated IgE antibody (in other word, the antibody binds more strongly to heated IgE antibody).

According to the present invention, provided is an antibody that binds to a peptide having the amino acid sequence set forth in SEQ ID NO: 1 (NTNDWIEGETYYC), wherein the antibody binds to IgE antibody on the surface of B cell membrane and to heated IgE antibody. According to the present invention, provided is an antibody that binds to a peptide having the amino acid sequence set forth in SEQ ID NO: 11 (HHHHHHGGSGGSDWIEGETYYC), wherein the antibody binds to IgE antibody on the surface of B cell membrane and to heated IgE antibody. In some embodiments, the antibody is an isolated monoclonal antibody. According to the present invention, provided is an antibody that binds to a peptide having the amino acid sequence set forth in SEQ ID NO: 18 (DWIEGETYYC), wherein the antibody binds to IgE antibody on the surface of B cell membrane and to heated IgE antibody. In some embodiments, the antibody is an isolated monoclonal antibody.

According to the present invention, provided is an isolated monoclonal antibody that completes with an antibody having a heavy chain variable region having the amino acid sequence set forth in SEQ ID NO: 8 and a light chain variable region having the amino acid sequence set forth in SEQ ID NO: 9, for binding to heated pathogenic IgE or IgE on B cell surface, or a peptide having the amino acid sequence set forth in SEQ ID NO: 11 (HHHHHHGGSGGSDWIEGETYYC). According to the present invention, provided is an isolated monoclonal antibody that completes with an antibody having a heavy chain variable region having the amino acid sequence set forth in SEQ ID NO: 8 and a light chain variable region having the amino acid sequence set forth in SEQ ID NO: 9, for binding to heated pathogenic IgE or IgE on B cell surface, or a peptide having the amino acid sequence set forth in SEQ ID NO: 18 (DWIEGETYYC).

The antibody that binds to the IgE antibody of the present invention can be obtained by, for example, immunizing an animal after connecting a peptide of 13 amino acid length of the amino acid sequence set forth in SEQ ID NO: 1 to a carrier protein. As the carrier protein, for example, keyhole limpet hemocyanin (KLH) can be used. The peptide and the carrier protein can be connected by use of, for example, 1-ethyl 1-3-[dimethylaminopropyl]carbodiimide hydrochloride (EDC). The connection of the peptide and the carrier protein may be expressed as a fusion protein thereof.

Whether an antibody binds to a peptide having the amino acid sequence set forth in SEQ ID NO: 1 (NTND-WIEGETYYC), or a peptide having the amino acid sequence set forth in SEQ ID NO: 11 (HHHHHHGGSGGSDWIEGETYYC) or a peptide having the amino acid sequence set forth in SEQ ID NO: 18 (DWIEGETYYC) can be confirmed by examining whether or not the antibody binds to the peptide immobilized to a solid phase via an appropriate spacer. Whether the antibody binds to the peptide immobilized to a solid phase can be detected by labeling a test antibody and bringing the antibody into contact with the peptide or bringing a test antibody into contact with the peptide and then using a labeled second antibody. Examples of the label include, but are not particularly limited to, a biotin label, a fluorescent label, an enzyme label and a radio isotope label. As the negative control, an isotype control antibody that does not react to a predetermined antigen can be used. The antibody can be varied depending on a subject to be given, and can be an antibody that binds to a peptide having the amino acid sequence corresponding to that set forth in SEQ ID NO: 1, 11 or 18 in a heavy chain amino acid sequence of the IgE antibody of the subject to be given.

Whether an antibody binds to IgE antibody on the surface of B cells can be confirmed by flow cytometry using IgE antibody-producing B cells. More specifically, a test antibody is tagged with a fluorescent label, brought into contact with IgE antibody-producing B cells; and then, whether the test antibody binds to the cells can be detected based on fluorescence by flow cytometry. When a test antibody is fluorescently labeled, if the antibody binds to cells, fluorescence derived from the fluorescent label of the antibody should be emitted from the cells. As a negative control, an isotype control antibody, which does not react with a predetermined antigen, can be used. In some embodiments, whether or not binding is made to IgE antibody on the surface of B cells stimulated can be confirmed.

Whether or not an antibody binds to IgE antibody on the surface of mast cells can be confirmed as follows. First, mast cells are brought into contact with IgE antibody to allow the IgE antibody to bind to FcɛRI on the surface of mast cells. For example, a test antibody is fluorescently labeled, brought into contact with mast cells having IgE antibody bound thereto, and subjected to flow cytometry. In this manner, whether or not the test antibody binds to the cells can be confirmed based on fluorescence. When the test antibody is fluorescently labeled, if the test antibody binds to cells, fluorescence derived from the fluorescent label of the antibody should be emitted from the cells. As a negative control, an isotype control antibody, which does not react with a predetermined antigen, can be used.

Whether an antibody binds to IgE antibody heated at 56° C. can be confirmed by heating IgE antibody at 56° C. for e.g., one to several hours, 10 to 20 minutes or 15 minutes and bringing the resultant IgE antibody into contact with a test antibody. More specifically, it can be detected by immobilizing heated IgE antibody to a solid phase and labeling a test antibody, then bringing into contact with the solid phase. Alternatively, a test antibody is brought into contact, and thereafter, a labeled secondary antibody can be used for detection. Examples of the label include, but are not particularly limited to, a biotin label, a fluorescent label, an enzyme labeling and radio isotope label. As a negative control, an isotype control antibody that does not react to a predetermined antigen, can be used.

Whether or not an antibody binds to IgE antibody before heating (non-heated IgE antibody) can be confirmed by, for example, keeping the IgE antibody, in the environment of 37° C. or less, and bringing the resultant IgE antibody into contact with a test antibody. More specifically, it can be detected by immobilizing non-heated IgE antibody to a solid phase, and bringing a test antibody into label and contact with the solid phase. Alternatively, a test antibody is brought into contact, and thereafter, a labeled secondary antibody can be used for detection. Examples of the label include, but are not particularly limited to, a biotin label, a fluorescent label, an enzyme labeling and radio isotope label. As a negative control, an isotype control antibody, which does not react with a predetermined antigen, can be used.

According to the present invention, the antibody that binds to IgE antibody has,
  a heavy chain variable region comprising heavy chain CDR1 having the amino acid sequence set forth in SEQ ID NO: 2, heavy chain CDR2 having the amino acid sequence set forth in SEQ ID NO: 3 and heavy chain CDR3 having the amino acid sequence set forth in SEQ ID NO: 4; and
  a light chain variable region comprising light chain CDR1 having the amino acid sequence set forth in SEQ ID NO: 5, light chain CDR2 having the amino acid sequence set forth in SEQ ID NO: 6 and light chain CDR3 having the amino acid sequence set forth in SEQ ID NO: 7.

According to the present invention, the antibody that binds to IgE antibody may have
  (i) A heavy chain having the amino acid sequence of a heavy chain variable region set forth in SEQ ID NO: 8 and a light chain having the amino acid sequence of a light chain variable region set forth in SEQ ID NO: 9. According to the present invention, (ii) the antibody that binds to IgE antibody may have a heavy chain having the amino acid sequence of a heavy chain set forth in SEQ ID NO: 8 and a light chain having the amino acid sequence of a light chain set forth in SEQ ID NO: 9.

Also, according to the present invention, the antibody that binds to IgE antibody may be an antibody that competes with the antibody that binds to IgE antibody described in (i) or (ii) mentioned in the above, for binding to IgE antibody. According to the present invention, the antibody that binds to IgE antibody may be an antibody that competes with the antibody that binds to IgE antibody described in (i) or (ii) mentioned in the above, for binding to a peptide having the amino acid sequence set forth in SEQ ID NO: 1, 11 or 18.

According to the present invention, the antibody that binds to IgE antibody may be a mammalian chimeric antibody or a mammalianized antibody, such as a canine chimeric antibody, caninized antibody, feline chimeric antibody or a felinized antibody, and used for administering to, e.g., a dog and a cat.

According to the present invention, the antibody that binds to IgE antibody may be a human chimeric antibody or a humanized antibody and used for administering to, e.g., a human.

According to the present invention, the antibody that binds to IgE antibody, if it is used for administering to a mammal, may be IgG1 antibody.

Whether or not an antibody has ADCC activity can be confirmed by using IgE antibody-producing B cells, effector cells and the antibody that binds to IgE antibody according to the present invention. As the effector cells, for example, mouse splenocytes, mononuclear cells separated from human peripheral blood or bone marrow, can be used. As the target cells, for example, IgE antibody-producing B cells can be used. The target cells are previously labeled with, e.g., $^{51}$Cr. To the target cells, the antibody of the present invention is added and the mixture is incubated. Thereafter, effector cells are added to the target cells in an appropriate ratio and the mixture is incubated. After incubation, the supernatant is taken, the number of labels in the supernatant are counted. In this manner, measurement can be made.

Whether or not an antibody has CDC activity can be confirmed by using a complement in place of effector cells used in an ADCC activity test.

In the present invention, the antibody that binds to IgE antibody or an IgE antibody-binding fragment thereof may be in a form of a drug-antibody conjugate (ADC) with a cytotoxic agent. As the cytotoxic agent, a cytotoxic agent using as an anti-cancer agent can be used. Examples of the cytotoxic agent include, chemotherapeutic agents (for example, anti-cancer agents such as commercially available anti-cancer agents including auristatin (auristatin E, auristatin F phenylenediamine (AFP), monomethyl auristatin E, monomethyl auristatin F and derivatives of these) and maytansinoid DM1 and DM4 and derivatives of these), camptothecin (SN-38, topotecan and exatecan and derivatives of these), DNA minorgroove binder (enediyne, lexitropsin, duocarmycin and derivatives of these), taxane (paclitaxel and docetaxel and derivatives of these), polyketide (discodermolide and a derivative thereof), anthraquinone (mitoxantrone and a derivative thereof), benzodiazepine (pyrrolobenzodiazepine, indolinobenzodiazepine and oxazolidinobenzodiazepine and derivatives of these), vinca alkaloid (vincristine, vinblastine, vindesine and vinorelbine and derivatives of these), doxorubicins (doxorubicin, morpholino doxorubicin and cyanomorpholino doxorubicin and derivatives of these), cardiac glycosides (digitoxin and a derivative thereof), calicheamicin, epothilone, cryptophicin, cemadotin, rhizoxin, netropsin, combretastatin, eleutherobin, etoposide, T67 (chulalik) and nocodazole), radioisotopes (for example, $^{32}$P, $^{60}$C, $^{90}$Y, $^{111}$In, $^{131}$I, $^{125}$I, $^{153}$Sm, $^{186}$Re, $^{188}$Re and $^{212}$Bi) and toxins (for example, diphtheria toxin A, pseudomonas endotoxin, ricin, saporin and the like). These can be used as a cytotoxic agent in ADC of the present invention. As the cytotoxic agent, any agent can be used as long as it is used for treating cancer. A cytotoxic agent and the antibody can be linked via a linker. A cytotoxic agent and a linker can be appropriately selected by those skilled in the art.

According to the present invention, the antibody that binds to IgE antibody can be used as a test reagent. In this case, the antibody that binds to IgE antibody may be any one of isotypes of antibodies.

According to the present invention, provided is a method of producing the antibody that binds to IgE antibody, comprising
  immunizing an animal (for example, a non-human animal, a non-human mammal, a bird) with a canine peptide having the amino acid sequence set forth in SEQ ID NO: 1 (NTNDWIEGETYYC).

According to the present invention, provided is a method for treating a disease or a condition associated with allergies in a subject in need thereof, comprising administering to the subject a therapeutically effective amount of an antibody that binds to the IgE antibody of the present invention.

According to the present invention, provided is a pharmaceutical composition comprising an antibody that binds to the IgE antibody of the present invention.

According to the present invention, provided is a pharmaceutical composition comprising a therapeutically effective amount of an antibody that binds to the IgE antibody of the present invention, for use in treating a disease or a condition associated with allergies. The antibody that binds to the IgE antibody according to the present invention specifically binds to IgE antibody on the surface of IgE antibody-producing B cells, thereby targeting the B cells. It is possible to suppress production of IgE antibody causing an allergic symptom by suppressing or killing the B cells. When an antibody that binds to the IgE antibody according to the present invention has low affinity to non-heated IgE antibody in the blood, the antibody reaches IgE antibody-producing B cells without being trapped by the IgE antibody in the blood. In this manner, the B cells can be suppressed or killed.

According to the present invention, provided is use of an antibody that binds to the IgE antibody according to the present invention in a manufacture of a pharmaceutical composition for use in treating a disease or a condition associated with allergies.

The pharmaceutical composition of the present invention may further comprise an excipient in addition to an antibody that binds to the IgE antibody according to the present invention. Examples of the excipient include, but are not limited to, water, saline, a phosphate buffer, dextrose, glycerol, a pharmaceutically acceptable organic solvent such as ethanol, collagen, polyvinyl alcohol, polyvinylpyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum Arabic, casein, agar, polyethylene glycol, diglycerin, glycerin, propylene glycol, vaseline, paraffin, stearyl alcohol, stearic acid, human serum albumin, mannitol, sorbitol, lactose and a surfactant.

The pharmaceutical composition of the present invention can be formed into various dosage forms such as a liquid (for example, injection), a dispersant, a suspension, a tablet, a pill, a powder and a suppository. A preferable embodiment is an injection, which is preferably administered by a parenteral route (for example, intravenous, percutaneous, intraperitoneal, intramuscular, transmucosal).

The pharmaceutical composition of the present invention may be provided in the form of a lyophilized formulation. The lyophilized formulation may be supplied together with sterile water for injection for preparing a drug solution when used.

The pharmaceutical composition of the present invention can be used in combination with other anti-allergic drugs. The pharmaceutical composition of the present invention may further contain other allergic drugs. The pharmaceutical composition of the present invention contains none of other allergic drugs and may be used in combination with other allergic drugs. In the present invention, provided is a combination drug of the pharmaceutical composition of the present invention and other allergic drugs. In the combination drug of the present invention, the pharmaceutical composition of the present invention and other allergy drugs may be contained in a same preparation or different preparations, respectively. In the combination drug of the present invention, the pharmaceutical composition of the present invention and other allergic drugs are contained in different preparations, respectively, these preparations may be simultaneously administered or successively or sequentially administered. Examples of the other anti-allergic drug include steroidal drugs (e.g., hydrocortisone, prednisolone, dexamethasone), antihistamine drugs (e.g., diphenhydramine, hydroxyzine, olopatadine, levocetirizine, cetirizine, clemastine fumarate, fexofenadine, loratadine), immunosuppressive drugs (e.g., cyclosporine, tacrolimus), immunotherapeutic drugs (standardized cedar pollen extract stock solution, recombinant type Der f 2-pullulan conjugate containing a Dermatophagoides *microceras* and Dermatophagoides *farina* extract, and the like), thromboxane A2 synthesis inhibitors (e.g., ozagrel hydrochloride hydrate), thromboxane A2 receptor antagonists (e.g., seratrodast, ramatroban), leukotriene receptor antagonists (e.g., montelukast sodium, pranlukast hydrate) and Th2 cytokine inhibitors (e.g., suplatast tosilate).

In an embodiment of the present invention, the pharmaceutical composition of the present invention can be used in combination with omalizumab.

According to the present invention, provided is a method of testing (or diagnosing) an allergic symptom or a risk of developing the symptom (or presence or absence of pathogenic IgE antibody) in a mammal, comprising
heating a biological sample obtained from a mammal to obtain IgE antibody that reacts to an antibody that binds to the IgE antibody according to the present invention (or heating a biological sample obtained from a mammal under conditions that provide a conformational change which allows for reacting to an antibody that binds to the IgE antibody according to the present invention), and
bringing the heated biological sample into contact with an antibody that binds to the IgE antibody or an antigen binding fragment thereof of the present invention. In the method of the present invention, the antibody that binds to the IgE antibody according to the present invention binds to heated IgE antibody; however, it has low affinity to non-heated IgE antibody in a specimen exhibiting a clinical symptom of allergy. Because of this, noise in diagnosis caused by non-pathogenic IgE antibody possibly present in the blood can be suppressed.

According to the present invention, severity of an allergic symptom can be evaluated in an individual having the allergic symptom by examining whether or not a mammal has pathogenic IgE antibody. Also, according to the present invention, a risk of developing an allergic symptom can be evaluated by examining whether or not a mammal has pathogenic IgE antibody. Accordingly, the method of the present invention can be a method for testing severity of an allergic symptom of a mammal having the allergic symptom. Further, the method of the present invention can be a method for testing a risk of developing an allergic symptom in a mammal.

In the method of the present invention, a biological sample is heated for the purpose of denaturing IgE antibody. Accordingly, the heating conditions for a biological sample are not particularly limited as long as IgE antibody is denatured and reacts to an antibody that binds to the IgE antibody according to the present invention; for example, heating at 56° C., for one to several hours, 10 to 20 minutes or 15 minutes can be employed.

The biological sample to be used in the method of the present invention is not particularly limited as long as it contains IgE antibody; for example, a tissue specimen containing IgE antibody or body fluid sample containing IgE antibody, such as blood, blood plasma, serum or tear, can be employed.

If the antibody that binds to the IgE antibody according to the present invention reacted to IgE antibody in a biological sample heated (in other words, a substance that reacts to an antibody that binds to the IgE antibody according to the present invention was present in a biological sample), it is possible to determine (or diagnose) that the subject, from which the biological sample is derived, has an allergic symptom.

The method of the present invention may further include a step of bringing a biological sample of a mammal before heating into contact with an antibody that binds to the IgE antibody according to the present invention. Thereby, if an antibody that binds to the IgE antibody of the present invention reacted to IgE antibody in a biological sample before heating (in other words, a substance that reacts to an antibody that binds to the IgE antibody according to the present invention was present in a biological sample), it is possible to determine that the subject, from which the biological sample is derived, contains IgE antibody, which does not make mast cells promote release of histamine. Thereby, although IgE antibody is present in the biological sample, if an antibody that binds to the IgE antibody according to the present invention does not react to IgE antibody in a biological sample before heating (in other words, a substance that reacts to an antibody that binds to the IgE antibody of the present invention is not present in a biological sample), the subject from which the biological sample is derived can be determined (or diagnosed) to have an allergic symptom.

The method of the present invention may further include comparing reactivity of an antibody that binds to the IgE antibody or an antigen binding fragment thereof according to the present invention to a biological sample obtained from a mammal, before and after heating. If the reactivity to IgE antibody contained in a biological sample does not change before and after heating (for example, a statistically significant difference is not observed in the reactivity before and after heating), it is possible to determine that the IgE antibody in a biological sample is IgE antibody that does not react to mast cells, or determine (or diagnose) that the subject, from which the biological sample is derived, does not have an allergic symptom clinically affecting health. If the reactivity to IgE antibody contained in a biological sample is accelerated by heating, it is possible to determine that the IgE antibody in a biological sample is IgE antibody reactive to mast cells, or determine (or diagnose) that the subject, from which the biological sample is derived, has an allergic symptom clinically affecting health. In this embodiment, enzyme hydrolyzing sugar chain, such as PNGaseF or EndoH, may be used in place of heating. The enzyme hydrolyzing sugar chain that can be used includes an enzyme enhancing binding property to 6C12 antibody when pathogenic IgE antibody treated with the enzyme is brought into contact with 6C12 in a non-heating condition. Particularly, the enzyme can be an enzyme decomposing an N type sugar chain between two sugar units selected from the group consisting of N-acetylglucosamine (GlcNAc) and mannose.

In the method of the present invention, for example, a healthy person (including an animal) having no clinical symptom of allergy can be used as a negative control. In the method of the present invention, for example, a patient (including an animal) having a clinical symptom of allergy can be used as a positive control. In the method of the present invention, whether or not a test subject has an allergic symptom may be determined in comparison with the positive control and/or negative control.

According to the present invention, provided is a diagnostic drug and a diagnostic kit comprising an antibody that binds to the IgE antibody of the present invention, for use in diagnosing an allergic symptom. In the diagnostic drug and the diagnostic kit of the present invention, a fluorescent dye, RI or an enzyme for labeling the antibody may be contained. In the diagnostic drug and the diagnostic kit of the present invention, a labeled secondary antibody may be contained. In the diagnostic kit of the present invention, one or all selected from the group consisting of a necessary buffer solution, a blocking solution, an enzyme reaction stop solution and a microplate reader may be contained.

The disclosures of all Patent Literatures and Non Patent Literatures cited in the specification are incorporated herein by reference in their entirety.

EXAMPLES

Example 1: Production of Anti-IgE Antibody

In the Example, an anti-IgE antibody was produced. Hereinafter, unless otherwise specified, the amino acid sequence of human IgE antibody is that registered in the GenBank under registration number: AH005278; the amino acid sequence of canine IgE antibody is that registered in the GenBank under registration number: L36872; the amino acid sequence of feline IgE antibody is that registered in the GenBank under registration number: AF162134; the amino acid sequence of a rat IgE antibody is that registered in the GenBank under registration number: K02901; and the amino acid sequence of a mouse IgE antibody is that registered in the GenBank under registration number: LC387253.

In order to prepare an anti-IgE antibody that cross-reacts to a wide variety of IgE antibodies of humans and animal species, a site of an amino acid sequence conserved among IgE antibody heavy-chain CH3 regions of a human, a dog, a mouse and a rat (amino acid sequence consisting of 13 amino acids at amino acid positions 282 to 294: $^{282}$NTND-WIEGETYYC$^{294}$ of a canine IgE antibody heavy chain constant region amino acid sequence information, GenBank AAA56797.1; set forth in SEQ ID NO: 1) was selected and a synthetic peptide for immunization was produced (see, FIG. 25). As shown in FIG. 25, the peptide sequence used for immunization including a peripheral area thereof has a homology among interspecies. Note that, the region of the peptide sequence shown in FIG. 25 is present in the CH3 region of IgE antibody, particularly in 4 discrete regions (regions at amino acid positions 213 to 217, amino acid positions 243 to 246, amino acid positions 274 to 276, and amino acid positions 305 to 308 in the amino acid information of a human IgE constant region, UniProtKB-P01854), which interact with IgE antibody receptor. When the constant region of one of the heavy chains of IgE antibody binds to an IgE antibody receptor in the amino acid region as mentioned above, the other constant region changes in conformation. Subsequently, the other constant region can bind to the IgE antibody receptor to which the one of the constant regions of the antibody binds at the first and fourth amino acid regions of the CH3 region. The IgE antibody thus bound to the IgE antibody receptor on the surface of mast cells changes in conformation of the heavy chain constant region. The conformational change is analogous to the conformational change of IgE antibody caused by heating.

A synthesized peptide was conjugated with KLH. After C57B16 mice were immunized with the conjugate, iliac lymph node cells were taken and fused with mouse myeloma cell strain SP2 to prepare hybridomas. Antibodies that react to rat IgE (Invitrogen) and canine IgE (Bethyl Laboratories, Inc.) were selected by two-stage screening to obtain a hybridoma clone (6C12, mouse IgG1κ).

6C12-producing hybridomas were intraperitoneally injected in pristane-treated Balb/c mice at a ratio of 1×10$^6$ cells/mouse, in accordance with a routine method. Two to three weeks later, the ascites was collected and subjected to affinity chromatography using a Protein G column (GE Healthcare) to purify monoclonal antibodies. In the specification, the monoclonal antibody produced from 6C12 clone obtained from the clone is simply referred to as "6C12".

Example 2: Analysis of Properties of Anti-IgE Monoclonal Antibody Obtained

Purified 6C12 was labeled with biotin. The reactivity thereof to each of IgE antibodies of the animal species was analyzed by establishing the ELISA system. ELISA system was constructed by using a 96-well black microplate (Greiner) for ELISA. First, IgE antibody and IgG antibody were diluted with a phosphate buffer and immobilized to the microplate. The IgE antibody and IgG antibody used for immobilization are as follows: canine IgE (Bethyl Laboratories, Inc.), a human IgE (Millipore), rat IgE (Invitrogen), and mouse IgE (BD Phamingen). Also, a recombinant cat IgE protein purified from a silkworm body fluid (see, Griot-Wenket et al., 2000, Vet. Immunol. Immunopathol., 75:59-69), canine IgG (Cappel), a human IgG (Millipore) and feline IgG (Bethyl Laboratorie, Inc.), which were separately prepared, were put in use. Immobilization was carried out at 4° C., overnight.

To the plate used for immobilization, a blocking treatment was applied with a blocking buffer (1% fish gelatin containing phosphate buffer) at 4° C., overnight and a reaction was carried out with a biotin-labeled purified 6C12 diluted with the same buffer up to a concentration of 0.5 μg/ml, at room temperature for 2 hours. After completion of washing with PBS-T (0.05% Tween 20-containing phosphate buffer solution), a reaction with streptavidin-β-galactosidase was carried out at room temperature for 2 hours. After washing, a solution of a substrate for β-galactosidase, i.e., 4MU (4-methylumveriferyl β-D-galactopyranoside) was added. After a reaction was carried out for one hour, an enzyme reaction stop solution, i.e., 0.25 M $Na_2CO_3$, was added to terminate the reaction. The (fluorescence) intensity of a fluorescent substance generated by the decomposition with the enzyme was measured by a fluorescent plate reader (excitation wavelength 355 nm, fluorescence wavelength 460 nm, cutoff wavelength 455 nm).

Figure 2:
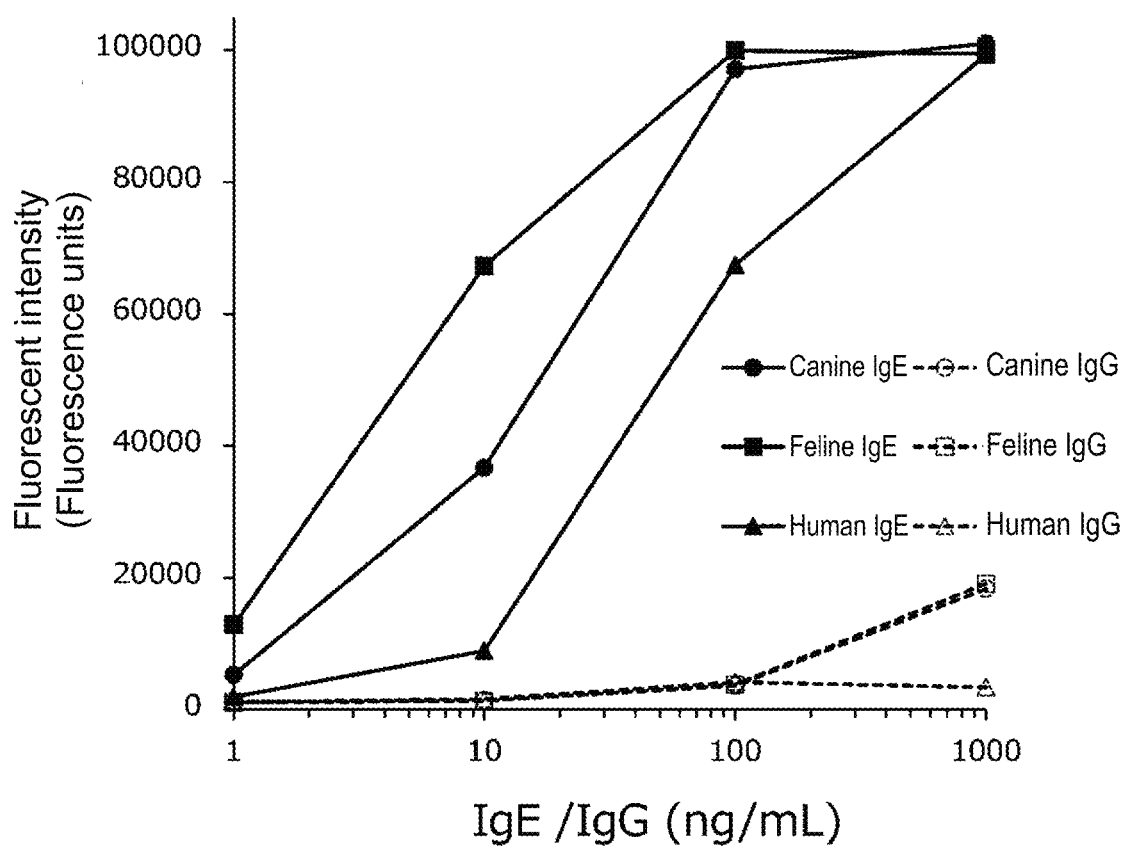
FIG. 2 shows that the anti-IgE antibody of the present invention does not substantially bind to IgG antibodies of various mammals.

The results were as shown in FIG. 1 and FIG. 2. As shown in FIG. 1, purified 6C12 reacted to canine IgE, human IgE, rat IgE, recombinant feline IgE protein. Whereas, as shown in FIG. 2, no reaction was observed in human, canine and feline IgG. From these results, it was demonstrated that 6C12 is an antibody that specifically binds to IgE antibody. However, the IgE antibodies used in the Example were produced by, e.g., culture cells and cancer cells, and thus considered to have a three-dimensional conformation different from that of a non-heated IgE antibody obtained from a living body having a clinical symptom of allergy.

From the above, it was estimated that the site recognized by 6C12 is commonly present in canine, human, rat and feline peptides used for immunization (see, FIG. 25).

Example 3: Relationship Between Anti-IgE Monoclonal Antibody Obtained and Conformational Change of IgE Antibody In the Example, the relationship between the anti-IgE monoclonal antibody obtained and a conformational change of IgE antibody was examined.

Using antigen-specific IgE antibody quantification, ELISA, employing the above IgE antibody measurement ELISA, a Der f 2-IgE antibody (more specifically, IgE antibody that binds to Der f 2) in the canine serum was examined. As the antigen, one of major allergens of Dermatophagoides *Farinae*, Der f 2 (recombinant protein produced by using silkworm and provided by Nippon Zenyaku Kogyo Co., Ltd.) was used. The serum samples used herein were 41 serum samples (clinical-case serum) of dogs conceivably developing clinical symptoms of allergies and 9 serum samples (experimental canine serum samples) obtained by immunizing experimental beagles by subcutaneously injection of Der f 2 and alum adjuvant twice or more.

Figure 4:
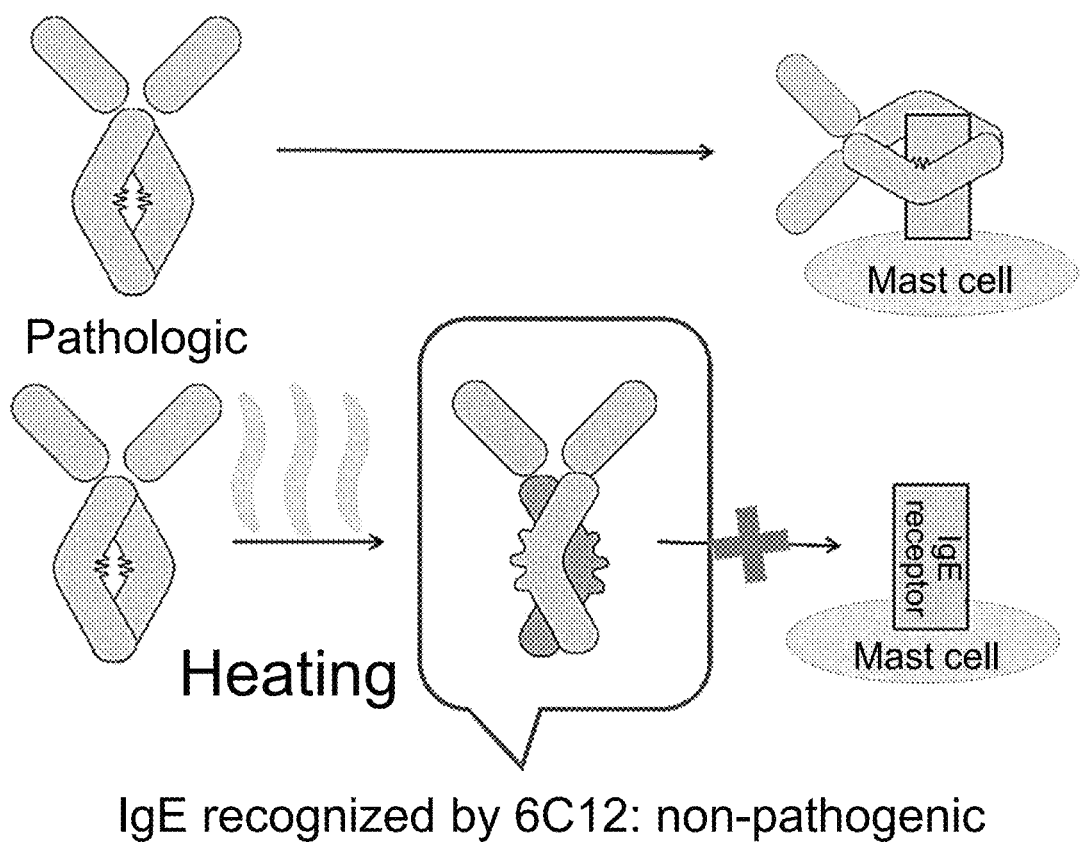
FIG. 4 shows that non-heated IgE antibody binds to FcεRI on the surface of mast cells; whereas IgE antibody changed in conformation by heating does not bind to FcεRI; and illustrates that the anti-IgE antibody of the present invention specifically binds to IgE antibody changed in conformation by heating.

Measurement Der f 2-IgE antibody in serum was carried out as follows. To the same ELISA plate as mentioned above, Der f 2 was immobilized at a ratio of 1 µg/ml and blocked at room temperature for 2 hours. Then, the serum diluted up to 200 fold with a blocking buffer was added and allowed to react at 4° C. overnight. Thereafter, biotinylated 6C12 was allowed to react. The fluorescence intensity of a fluorescence substance generated by the reaction between streptavidin-β-galactosidase and 4MU was measured in the same manner as above. A recombinant feline IgE antibody was diluted to various concentrations with a 200-fold dilution solution of normal canine serum and measured to prepare a standard curve based on the above feline IgE recombinant protein as a standard. The concentration of Der f 2-IgE in each of the clinical-case serum and experimental canine serum was quantitatively measured. As a result, as shown in FIG. 3, IgE antibody was not virtually detected in the clinical-case serum; whereas, in the experimental canine serum, a high IgE value was detected. Since it has long been known, from previous studies, that the serum IgE, if it is heated at 56° C., changes in three-dimensional conformation and fails to bind to an IgE antibody receptor (see, FIG. 4), the serum before measurement was heated at 56° C. for 15 minutes in order to change the three-dimensional conformation of the antibody and again subjected to measurement of IgE antibody by 6C12. As a result, as shown in FIG. 3, a high level of IgE antibody was detected in the clinical case serum. Note that, it is known that heated IgE antibody cannot bind to FcεRI on the surface of mast cells and does not contribute to degranulation by the mast cells.

Figure 5:
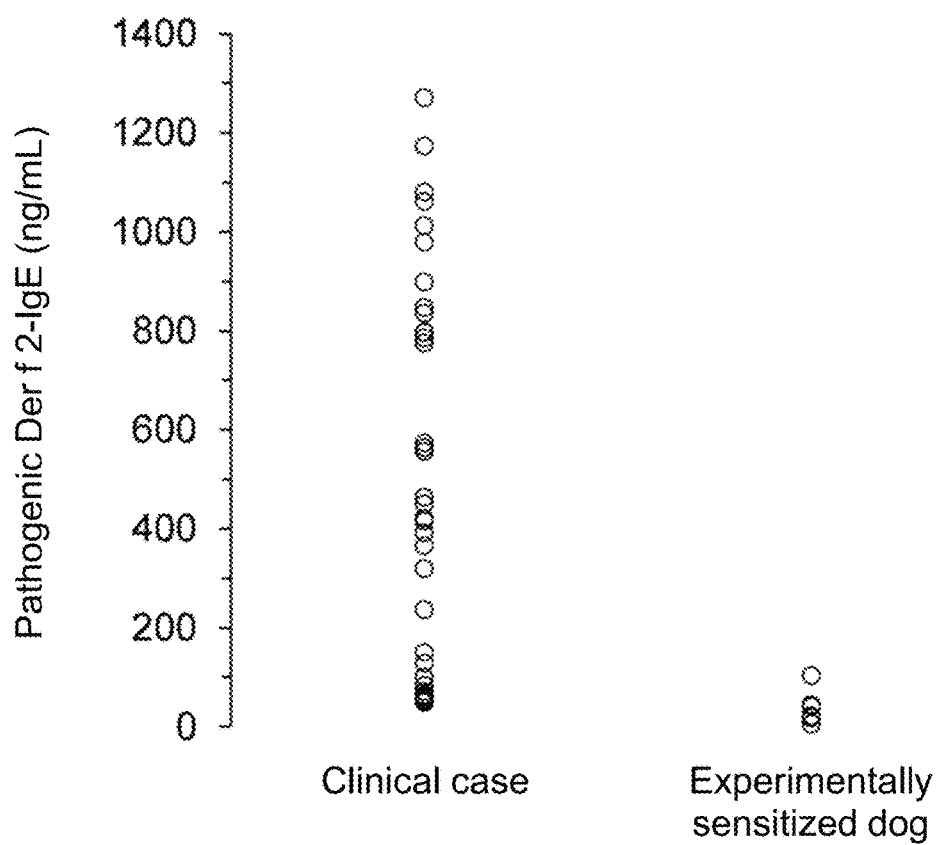
FIG. 5 shows that the serum concentration of the IgE antibody that can bind to FcεRI on the surface of mast cells (the amount of pathogenic IgE antibody) can be obtained by subtracting the IgE antibody level, which is measured by using the IgE antibody of the present invention, before heating from that after heating.

When the measurement values of the IgE antibody before and after heating are compared, it was confirmed that the IgE antibody levels of all clinical-case serum samples are significantly different (49-1271 ng/ml, average value 447 ng/ml, median 392 ng/ml) as shown in FIG. 5; whereas, the difference in antibody level of the experimental canine serum was only low (0-103 ng/ml, average value 26 ng/ml, median 18 ng/ml). From the results, it was found that 6C12 recognizes IgE antibody depending on the three-dimensional conformational change. It was also found that in the clinical-case serum samples of the allergic dogs, a large amount of IgE antibody before conformational change by heating is present; whereas, a large amount of IgE antibody originally changed in conformation is present in the experimental canine serum samples.

From the above results, the followings were considered. The development of allergic symptoms or the results of an allergic reaction test (prick test, intradermal reaction) on patient's skin correlates only weakly with the IgE antibody level measured in the serum. The weak correlation has long been a problem (see, for example, Bryant, D. H. et al., 1975, Clin. Allergy, 5:145-157). Also the inventors empirically learned that experimental dogs even though their IgE antibody levels in the serum are extremely high, rarely develop allergic symptoms or do not show a positive reaction in the intradermal reaction (an allergen was intradermally injected to observe formation of wheal). This was considered because the IgE antibody (hereinafter referred to as pathogenic IgE antibody) responsible for the development of the symptoms is not produced. It was previously found, not only in experiments using mouse IgE (Wyczolkowska, J. and Prouvost-Danon, A., 1976, Int. Arch. Allergy Appl. Immunol., 50:43-54) but also in cases using the IgE antibody of human allergic patient's serum (Solley, G. O. et al., 1976, J. Clin. Invest., 58:408-420), that the three-dimensional conformation of IgE antibody is changed by heating the serum, with the result that the IgE antibody fails to bind to an IgE antibody receptor (FcεRI) of the surface of mast cells, causing no allergic reaction. Since the IgE antibody denatured with heat can be detected by 6C12, the IgE antibody detected by 6C12 is estimated as the IgE antibody denatured, which was considered as non-pathogenic IgE antibody that does not bind to mast cells. From our experimental results, it was considered that the IgE antibody contained in clinical-case serum samples of allergic dogs is pathogenic IgE antibody whose three-dimensional conformation can be changed; whereas, the IgE antibody experimentally induced by sensitization is non-pathogenic IgE antibody. The phenomenon where the discrepancy between IgE antibody and development of allergic symptoms can be solved by 6C12, can be recognized.

The same phenomenon was seen in cats. When feline IgE antibody was measured by replacing the above IgE antibody measurement system with the feline serum and replacing the immobilized allergen from Der f 2 to Dermatophagoides

*Farinae*, IgE antibody was detected after heating. Similarly to the case of dogs, pathogenic IgE antibody was successfully detected (Table 1). From the results, it was confirmed that the phenomenon observed in the dogs was observed in cats, and is considered to be commonly applied to whole animal species including a human.

TABLE 1

TABLE 1: 6C12 recognizes heated IgE

|  | Before heating | After heating | Pathogenic IgE |
|---|---|---|---|
| Allergy case, Cat 1 | 0 ng/ml | 89 ng/ml | 89 ng/ml |
| Allergy case, Cat 2 | 0 ng/ml | 34 ng/ml | 34 ng/ml |
| Allergy case, Cat 3 | 0 ng/ml | 91 ng/ml | 91 ng/ml |

Example 4: Cell Specificity of Obtained Anti-IgE Antibody

IgE is present in free form in the blood and expressed on B cell surface and mast cell surface. In the Example, the anti-IgE antibodies obtained were subjected to cell-specificity evaluation.

The peripheral blood mononuclear cells of a dog clinically suspected of having an allergy symptom were cultured in RPMI1640 medium containing 10% fetal bovine serum and 1 µg/ml concanavalin A (ConA), at 37° C. for 3 days, and stained with an anti-CD21 antibody (Bio-Rad) used as a canine B-cell marker, simultaneously with a commercially available anti-canine IgE mouse monoclonal antibody (clone E6-71A1) or 6C12. B cells having IgE antibody on the cell surface were analyzed by flow cytometry. The results were as shown in FIG. 6.

Figure 6:
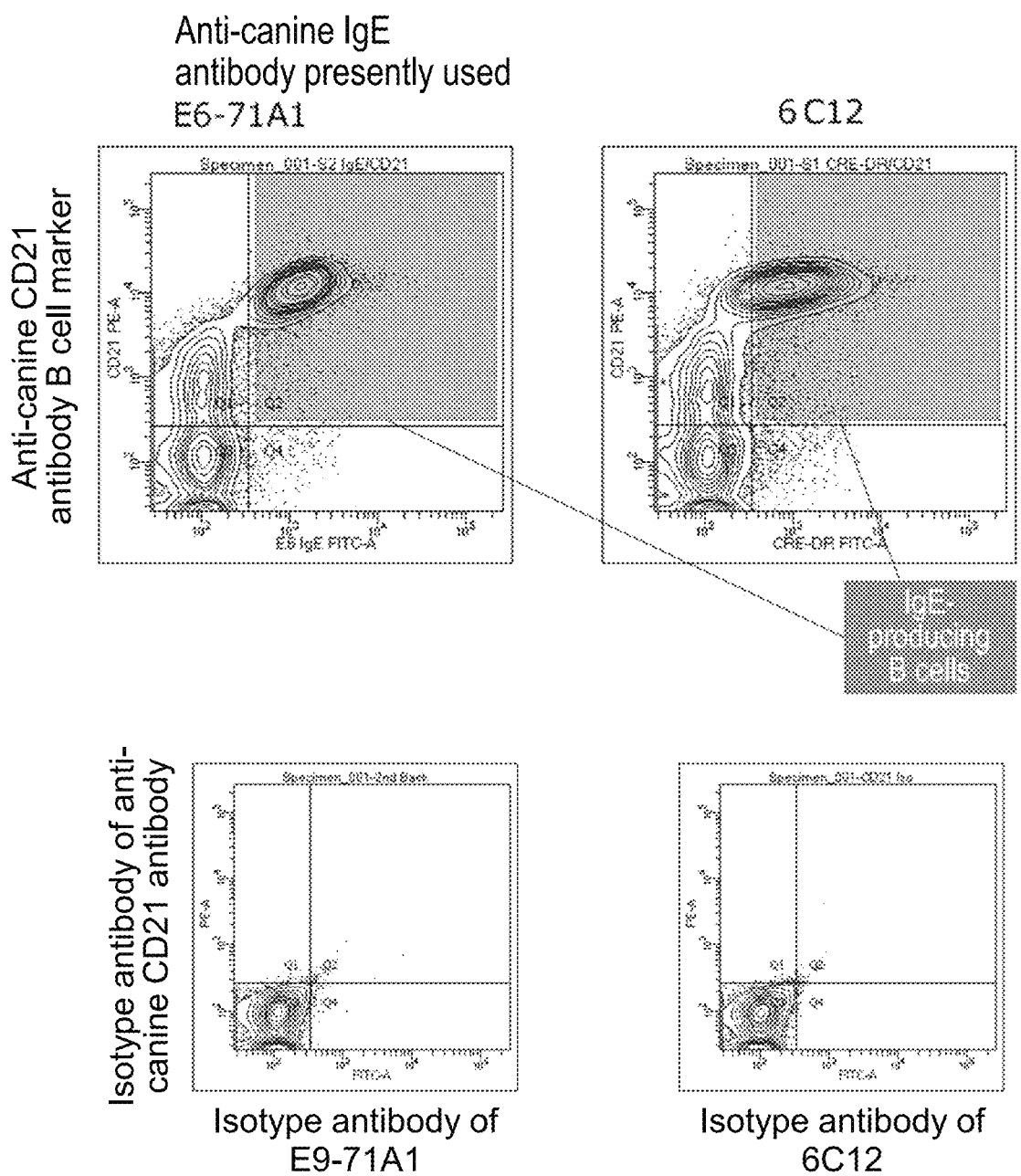
FIG. 6 shows that the anti-IgE antibody of the present invention binds to IgE antibody-producing B cells.

As shown in FIG. 6, it was found that B cells expressing IgE antibody can be detected by 6C12, similarly to E6-71A1. From the finding, 6C12 can be used for detecting IgE antibody-producing B cells, and thus, applied to an antibody medicine eliminating IgE antibody-producing B cells. Since 6C12 does not bind to pathogenic IgE antibody in the blood, when 6C12 as an antibody drug is administered, the antibody drug (administered) conceivably reaches IgE antibody-producing B cells directly without being absorbed by IgE antibody in the blood. Compared to a previously developed antibody drug (quilizumab) that targets IgE antibody-producing B cells and reacts to IgE antibody in the blood (Harris, J. M. et al., 2016, Respir. Res., 17:29), it is suggested that the antibody obtained herein has a significant usefulness (over previously existing antibodies).

Figure 7:
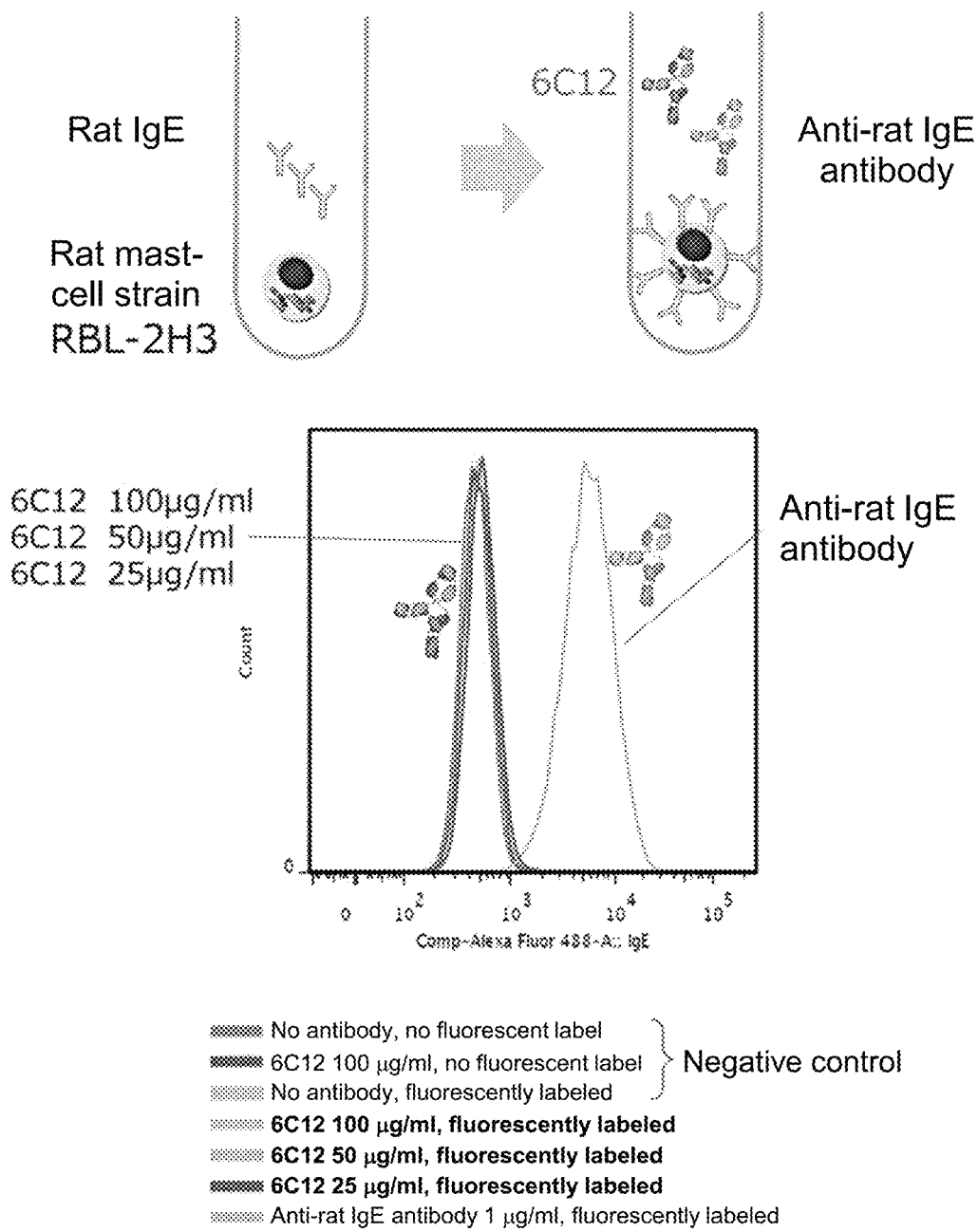
FIG. 7 shows that the anti-IgE antibody of the present invention does not bind to IgE antibody bound to FcεRI of mast cells, in vitro.

Subsequently, the reactivity of an antibody to IgE antibody on the mast-cell surface was evaluated. The reactivity to IgE antibody on the mast-cell surface was first examined in vitro. To rat mast-cell strain RBL-2H3, rat IgE (Invitrogen) was added and allowed to bind to FcεRI on the RB-2H3 surface. To this, 6C12 fluorescently labeled with fluorescein isothiocyanate (FITC) was added and the reactivity thereof was confirmed by flow cytometry. As a result, as shown in FIG. 7, it was confirmed that the rat IgE antibody is bound to the RBL-2H3 surface by using the FITC labeled anti-rat IgE antibody. However, even if the added concentration of 6C12 increases, the fluorescence intensity was maintained at the same level as that of a negative control. 6C12 did not bind to the IgE antibody on the RBL-2H3 surface. IgE antibody was known to change in conformation when it binds to FcεRI of mast cells. Thus, it was considered that 6C12 antibody cannot bind to the IgE antibody due to such a conformational change.

Figure 8:
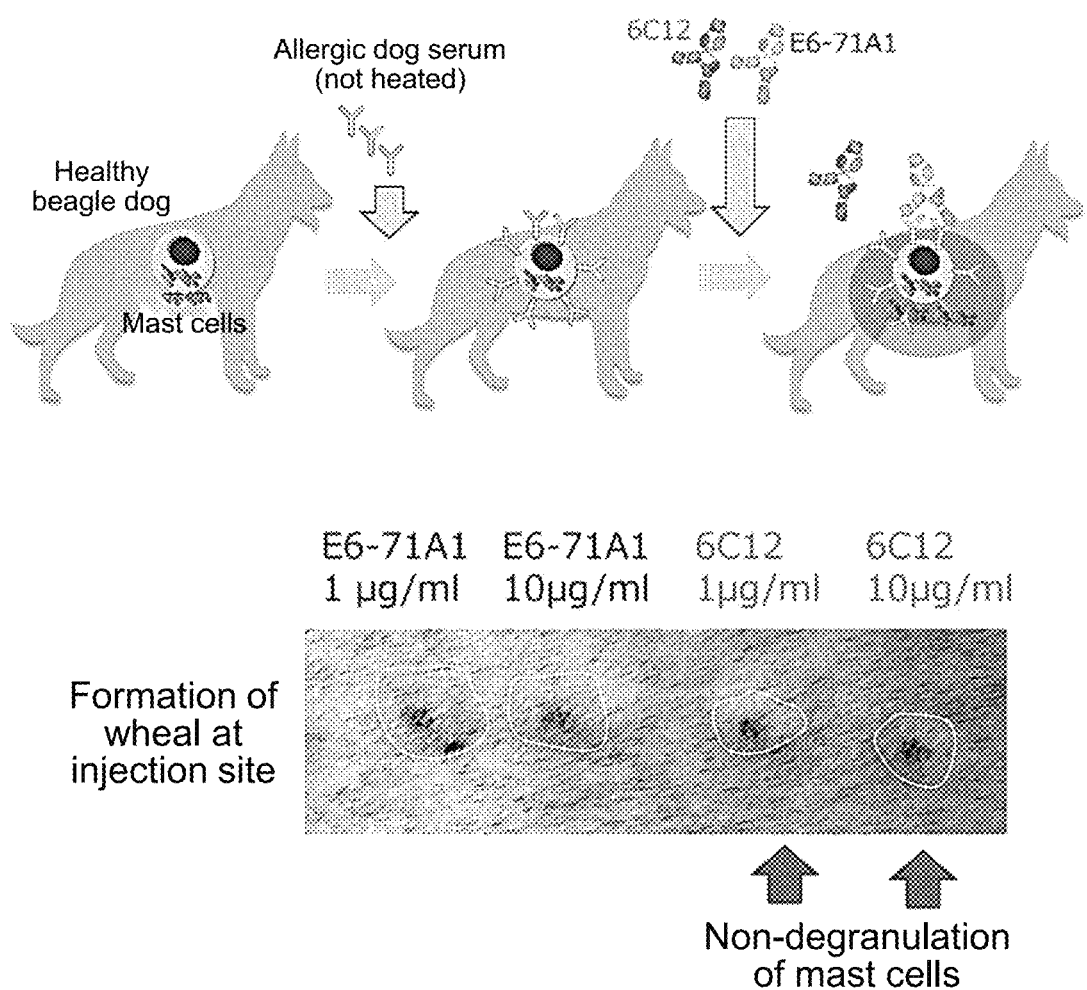
FIG. 8 shows that the anti-IgE antibody of the present invention does not form a crosslink with IgE on mast cells in vivo to inhibit degranulation of mast cells, thereby preventing induction of an allergic inflammatory reaction (wheal formation).

Next, the reactivity of an antibody was evaluated by using normal mast cells in vivo. Using the Prausnitz-Kustner test for sensitizing skin mast-cells of a healthy dog to IgE antibody by intradermally injecting the serum of an allergic dog, the reactivity of 6C12 to IgE antibody on the surface of normal mast cells was examined. After the concentration of IgE antibody in allergic dog's serum was adjusted to be 300 ng/ml, 0.05 ml of the serum was intradermally injected to sites in the breast of a healthy beagle dog. Twenty four hours later, 0.05 ml of 6C12 and anti-dog IgE antibody (clone E6-71A1) were injected intradermally at 1 µ/ml and 10 µ/ml, respectively, in the same sites. In all of the sites where E6-71A1 was injected, wheal formation was observed, which is an evidence that E6-71A1 bound onto mast cells (when two IgE molecules are "crosslinked" with E6-71A1 on the mast cell, the mast cell is degranulated and inflammation occurs); however, no wheal formation was observed in the case of 6C12 (FIG. 8). From the results, it was demonstrated in vitro and in vivo that 6C12 does not bind to IgE antibody on mast cells. From this, it was found that the anti-IgE antibody obtained does not induce degranulation of mast cells; and that if 6C12 is administered as an antibody drug to allergic patients, 6C12 does not bind to IgE antibody on mast cells and causes no anaphylactic shock.

As described above, it was found that 6C12 recognizes IgE antibody-producing B cells and does not recognize IgE antibody (live, non-heated state, pathogenic) in the blood or IgE antibody on the surface of mast cells. More specifically, 6C12 has the following binding specificities.

TABLE 2

TABLE 2: Binding specificity of 6C12 to IgE antibody

| Binding partner | Binding property |
|---|---|
| Non-heated IgE antibody in clinical allergic specimen | Not bind |
| Heated IgE antibody in clinical allergic specimen | Bind |
| IgE antibody on the surface of IgE antibody-producing B cells | Bind |
| IgE antibody on the surface of mast cells | Not bind |

From the above Example, it was found that when 6C12 is used for tests of IgE antibody in heated and non-heated serum, pathogenic IgE antibody causing conformational change can be detected; and that the antibody of the present invention can be used in an inflammation test using IgE antibody as an index. It was also suggested that the antibody of the present invention can be developed into an antibody medicine and used as a fundamental allergy therapeutic agent for excluding IgE antibody-producing B cells from the body. As an anti-human IgE antibody drug presently in use, omalizumab (Zheng, L. et al., 2008, Biochem. Biophys. Res. Commun., 375:619-622) and quilizumab (Harris, J. M. et al., 2016, J. Allergy Clin. Immunol., 138:1730-1732; and Harris, J. M. et al., 2016, Respir. Res., 17:29) are known. The former drug is effective in reducing the level of IgE antibody in the blood but does not exclude IgE antibody-producing cells; however, the latter drug can exclude IgE antibody-producing cells but reacts to IgE antibody in the blood. Because of this, the higher IgE antibody level in the blood of an allergic patient, in other words, the stronger allergic symptom of a patient has, the lower (to one half) the effect becomes. However, an anti-IgE antibody drug using 6C12 can eliminate IgE antibody-producing cells without being interrupted by IgE antibody in the blood (see Table 2). Note that the recognition site by omalizumab is an IgE heavy chain constant region, $^{424}$HLP$^{426}$ ($^{305}$HLP$^{307}$ as the amino acid positions described in in Non Patent Literature 1 and the amino acid positions. described in UniProtKB-P01854), which is not overlapped with that by 6C12. Omalizumab is effective in reducing the IgE antibody level in the blood but cannot exclude IgE antibody-producing cells; whereas the antibody of the present invention, whose effect on reducing the IgE antibody level in the blood cannot be expected, can exclude IgE antibody-producing cells. Accordingly, the IgE antibody blood-level lowering effect can be obtained in synergy with an IgE antibody-producing cell removal effect by combination use of the antibody of the present invention and omalizumab.

Example 5: Production of Chimeric Antibody

In the Example, a recombinant mouse antibody (mouse IgG1κ) and a recombinant canine chimeric antibody were produced.

A gene for the IgG1 antibody variable region of a 6C12 producing hybridoma was analyzed to obtain the gene sequences of its heavy chain (see SEQ ID NO: 8) and light chain (K chain) (see SEQ ID NO: 9). Note that, in SEQ ID NO: 8, the amino acid positions 1 to 22 represents a signal sequence; the amino acid positions 23 to 179 represents a heavy chain variable region; and the amino acid positions 180 to 212 represents a heavy chain constant region. In SEQ ID NO: 9, the amino acid positions 1 to 22 represents a signal sequence; the amino acid positions 23 to 128 represents a light chain variable region; and the amino acid positions 129 to 174 represents a light chain constant region.

Figure 9:
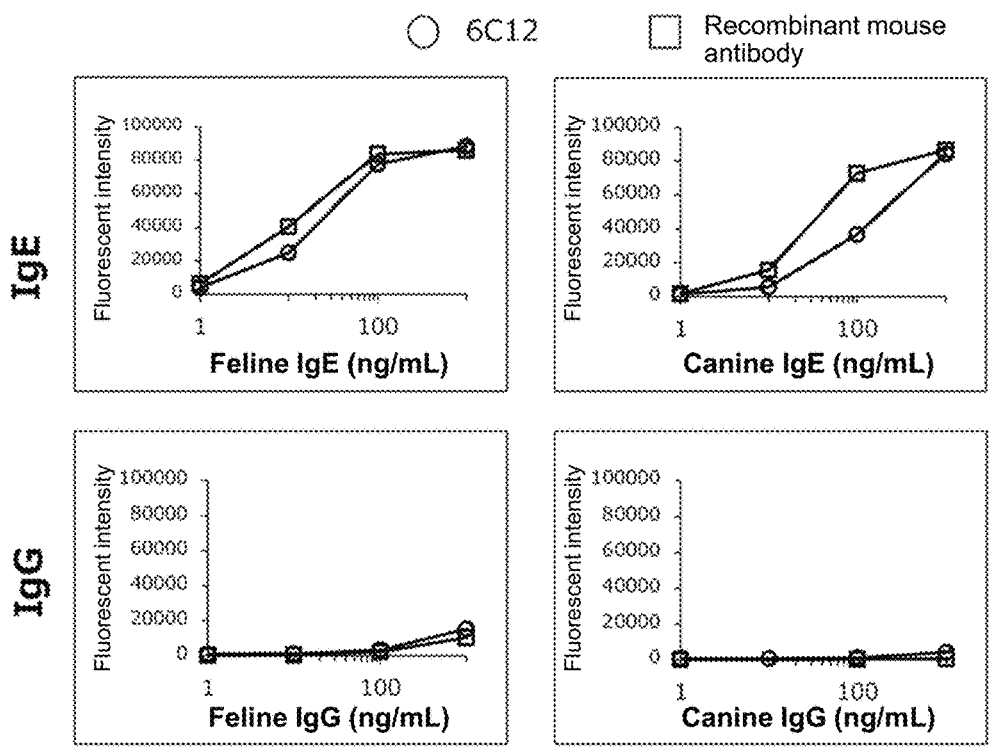
FIG. 9 shows reactivity of a recombinant mouse antibody of 6C12 antibody to IgE antibody and IgG antibody of a dog and a cat.

Based on the gene sequence and using a mouse IgG1 heavy-chain gene and k chain gene, a recombinant mouse antibody (mouse IgG1κ) of 6C12 was expressed in 293 cells and produced. The concentration of the antibody in the supernatant of the culture cells was measured and the antibody was subjected to experiments. The results were as shown in FIG. 9. When the reactions to the canine and feline IgE antibodies or IgG antibodies were examined, the recombinant mouse antibody did not react to the canine and feline IgG antibodies, and more highly reacted to canine and feline IgE antibodies than to 6C12.

Figure 10:
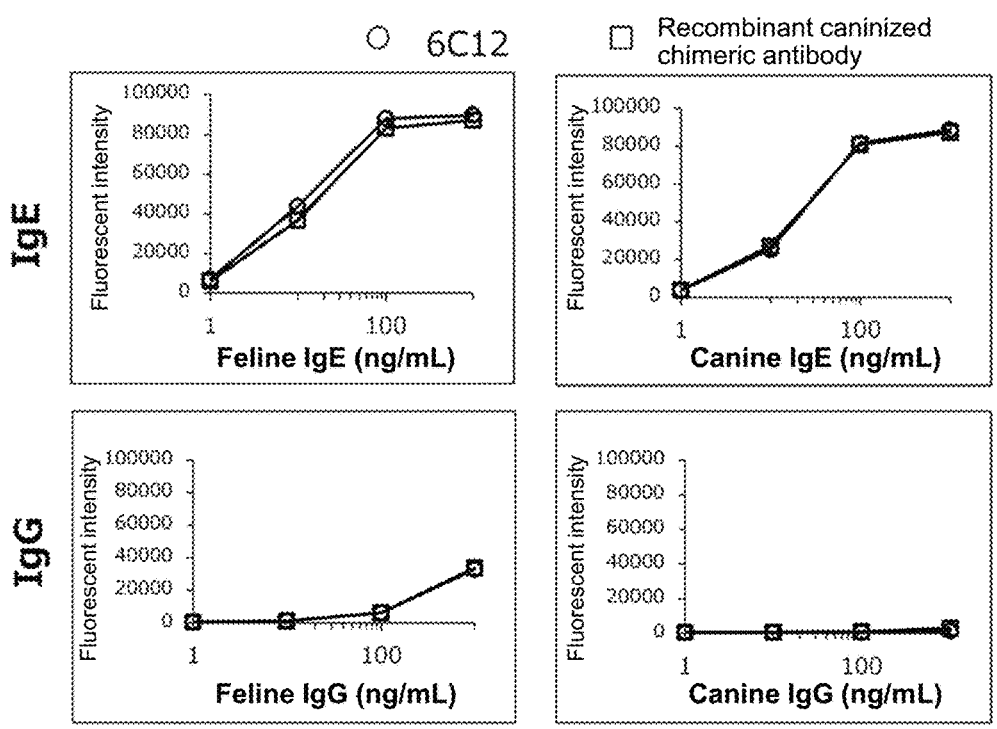
FIG. 10 shows reactivity of a canine chimeric antibody of 6C12 antibody to IgE antibody and IgG antibody of a dog and a cat.
Figure 11:
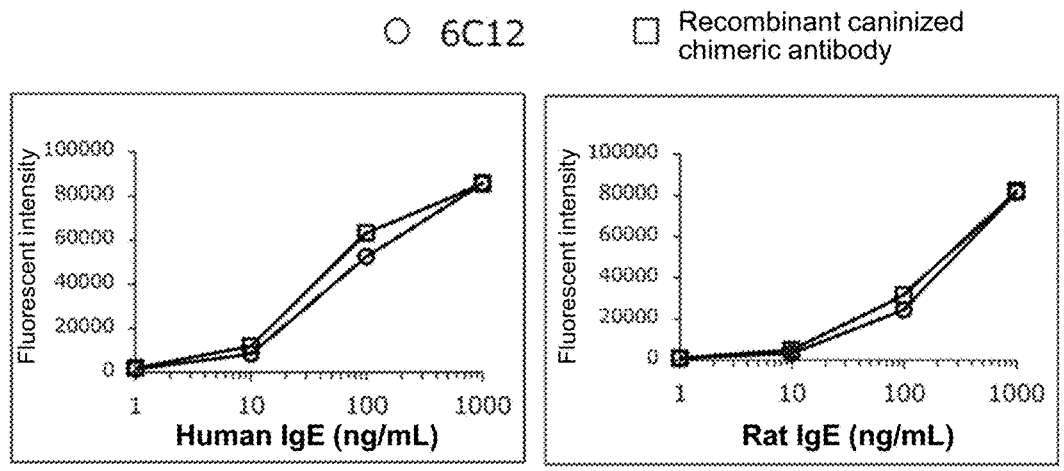
FIG. 11 shows reactivity of a canine chimeric antibody of 6C12 antibody to IgE antibody and IgG antibody of a human and a rat.

A canine IgGb gene (Tang, L. et al., 2001, Vet. Immunol. Immunopathol., 80:259-270) and a canine chimeric recombinant antibody were expressed in HEK293T cells to prepare the antibody. The culture supernatant was subjected to affinity purification using a protein A column to recover a recombinant antibody, which was subjected to experiments. The results were as shown in FIG. 10. The recombinant caninized chimeric antibody had the same reactivity to canine and feline IgE antibodies as that of 6012 and did not react to canine and feline IgG antibodies. As shown in FIG. 11, it was found that the caninized chimeric antibody has the same reactivity to human IgE antibody and rat IgE antibody as that of 6C12. Accordingly, it was found that the recombinant antibody produced from 6C12 maintains the same reactivity as in 6012 and can be used as an antibody drug.

According to the Example, it is considered the epitope of 6C12 antibody is present in the state where it can bind to 6012 in heated IgE antibody and membrane-bound IgE antibody on the surface of B cells, and present in the state where it cannot bind to 6012 in membrane-bound IgE antibody on the surface of mast cells. Since the 6012 antibody was obtained when a peptide consisting of the amino acid sequence set forth in SEQ ID NO: 1 was used as an immunogen, it is found that an antibody that binds to heated IgE antibody and/or membrane-bound IgE antibody on the surface of B cells and does not bind to membrane-bound IgE antibody on the surface of the mast cells, can be obtained by using a peptide consisting of the amino acid sequence set forth in SEQ ID NO: 1 as an immunogen.

Example 6: Animal Test of the Anti-IgE Antibody of the Present Invention

The anti-IgE antibody of the present invention 6C12 did not react to IgE antibody in a non-heated specimen exhibiting a clinical symptom of allergy and reacted to the IgE antibody in a heated specimen. In contrast, the anti-IgE antibody of the present invention bound to the IgE antibody in a specimen experimentally sensitized by subcutaneously injecting an allergen, before and after heating. From the results, in the above Example, it was considered that 6C12 cannot bind to IgE antibody (pathogenic IgE antibody) before heating, which can bind to mast cells, and can bind to IgE antibody (heated IgE antibody and IgE antibody of an experimentally sensitized specimen) which cannot bind to mast cells.

First, two specimens of canine serum samples were selected by using 6C12. More specifically, as the specimens containing pathogenic IgE antibody, a specimen in which 6012 did not react to the serum before heating (Der f 2-IgE concentration was 0 ng/ml) and reacted to the serum after heating (Der f 2-IgE concentration was 848 ng/ml) was selected. As the specimen containing non-pathogenic IgE antibody, a specimen in which 6C12 reacts equivalently to the serum samples before and after heating (Der f 2-IgE concentration before heating was 1054 ng/ml, that after heating was 1052 ng/ml) was selected.

Figure 12:
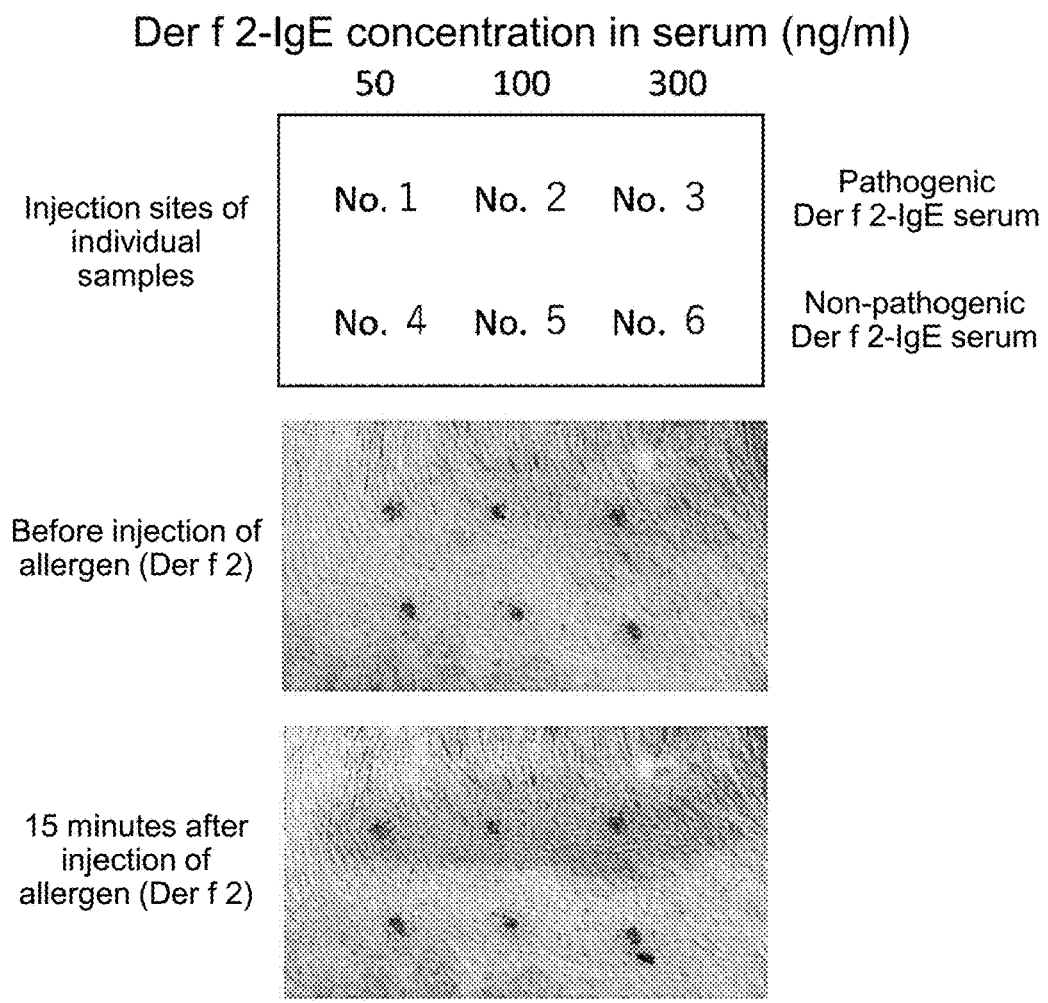
FIG. 12 shows that pathogenic IgE causes an allergic reaction and non-pathogenic IgE does not cause an allergic reaction in vivo. A single serum sample of a disease-dog containing pathogenic IgE alone and a single serum sample of an experimentally sensitized dog containing non-pathogenic IgE alone were selected from the serum samples used in the experiment shown in FIG. 5, diluted to various concentrations and injected to the skin of healthy dogs. After twenty-four hours, allergen (Der f 2) was intradermally injected into the same injection site. Whether or not each of the IgE binds to mast cells was determined by the formation of wheal. It is shown that the pathogenic IgE binds to mast cells to form wheal against Der f2, but the non-pathogenic IgE does not bind to mast cells and thus does not form wheal.

To the sites of a beagle dog shown in the upper stage of FIG. 12,

No. 1: IgE antibody (50 ng/ml) obtained from a specimen containing pathogenic IgE antibody No. 2: IgE antibody (100 ng/ml) obtained from a specimen containing pathogenic IgE antibody No. 3: IgE antibody (300 ng/ml) obtained from a specimen containing pathogenic IgE antibody No. 4: IgE antibody (50 ng/ml) obtained from a specimen containing non-pathogenic IgE antibody No. 5: IgE antibody (100 ng/ml) obtained from a specimen containing non-pathogenic IgE antibody and No. 6: IgE antibody (300 ng/ml) obtained from a specimen containing non-pathogenic IgE antibody were intradermally injected, respectively (Day 1).

Twenty four hours later, an allergen to which the IgE antibody was reacted, was intradermally administered (Day 2). More specifically, Der f 2 (sample diluted to 10 μg/mL when used) was intradermally administered. Fifteen minutes later, an allergic symptom was evaluated based on the diameter (mm), hardness (1: no wheal, 2: soft, 3: hard) and redness (1: none, 2: mild, 3: strong) of wheal.

The results were as shown in FIG. 12. As shown in FIG. 12, wheal and redness were observed only in the sites injected with the IgE antibodies obtained from the specimen described in Nos. 1 to 3 in the above. The evaluation results of allergic symptoms were as shown in Table 3.

TABLE 3

TABLE 3: Evaluation results of allergic symptom

|  | No. 1 | No. 2 | No. 3 | No. 4 | No. 5 | No. 6 |
|---|---|---|---|---|---|---|
| Diameter (mm) | 15 | 15 | 20 | 0 | 0 | 0 |
| Hardness | 2 | 2 | 2 | 1 | 1 | 1 |
| Redness | 3 | 3 | 3 | 2 | 1 | 1 |

From the above, it was considered that 6C12 is useful to determine that pathogenic IgE antibody is present.

Example 7A: Cytotoxicity of an IgE-Producing B-Cell Tumor Cell Strain

Figure 13:
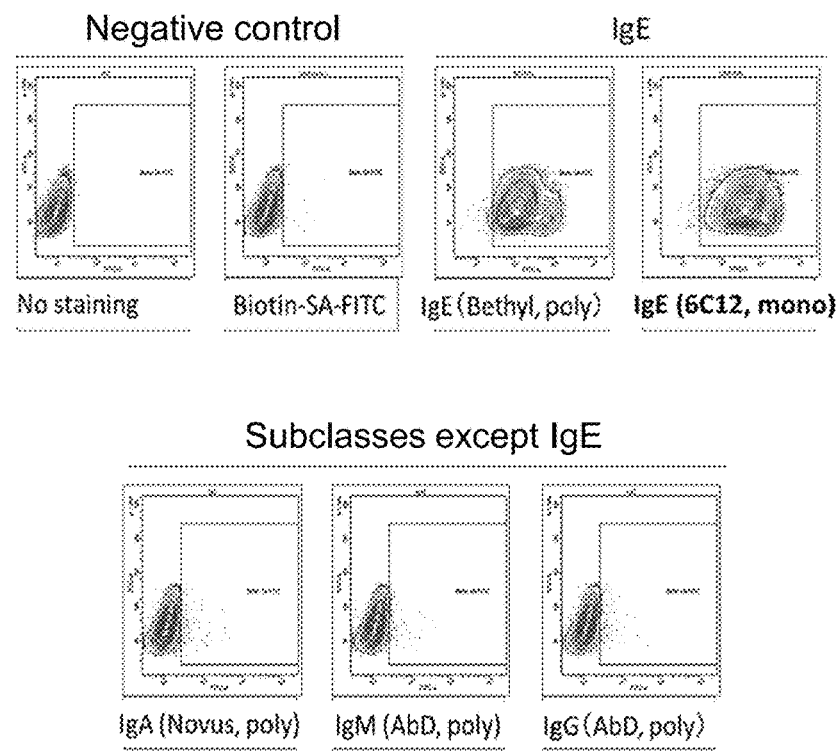
FIG. 13 shows the binding property of 6C12 antibody to matured IgE antibody-producing B cells.

From the blood of a dog (13 years old, species: Yorkshire terrier, castrated male) suspected of having a lymphoma, peripheral blood mononuclear cells were separated by Ficoll gradient centrifugation in accordance with a routine method, and thereafter, subcultured in RPMI-1640 containing 10% fetal bovine serum, for 6 months or more. As a result, tumor cells continuously proliferating were obtained. The type of antibody on the surface of tumor cells was examined by using various antibodies for a dog in accordance with flow cytometry. The antibodies used for the examination are an anti-canine IgM goat polyclonal antibody (Novus Biologicals), an anti-canine IgG sheep polyclonal antibody (AbD Serotec), an anti-canine IgA goat polyclonal antibody (AbD Serotec), an anti-canine IgE goat polyclonal antibody (Bethyl Laboratories) and 6C12. These antibodies were all labeled with biotin and put in use. These antibodies were added in a tumor cell suspension (50 μl) having a cell density of a 1×10$^6$ cells/ml so as to obtain a concentration of 500 μg/ml and allowed to react at 4° C. for 30 minutes and washed. Then, FITC-labeled streptavidin (BioLend) was added in a concentration of 500 μg/ml and allowed to react at 4° C. for 30 minutes. The stained cells were detected by FACS Canto II (Becton, Dikinson and Company). After the cells stained with Propidium Iodide (Propidium Iodide Staining Solution, Becton, Dikinson and Company), which was added in each cell suspension in an amount of 0.2 μL immediately before the analysis, were regarded as dead cells and removed, a cell population stained with the antibody used herein was detected. The analysis of the cell population was carried out by FACS Diva software (Becton, Dikinson and Company). As a result, it was found that the tumor cells are cells expressing only IgE on the cell surface thereof and not expressing other antibodies (i.e., IgM, IgG and IgA). From the results, the tumor cells were determined as a canine IgE-producing B cell tumor cell strain. As shown in FIG. 13, the IgE antibody effectively binds to the surface of IgE-producing B cells.

Next, cytotoxicity of IgE antibody was examined. By obtaining canine peripheral-blood mononuclear cells, effector cells were separated from the canine peripheral-blood in accordance with a routine method using Ficoll gradient centrifugation. To a canine IgE-producing B cell tumor cell strain (2.5×10$^4$ cells/well) used as a target cell, the chimeric antibody or control canine antibody prepared in the above Example was allowed to react in a concentration of 10 ng/ml for 30 minutes. Thereafter, the canine peripheral blood mononuclear cells (1.25×10$^5$ cells) were added in each well, and cultured for 5 hours. The culture medium was collected and the concentration of lactose dehydrogenase (LDH) in the medium was measured. LDH, which is an intracellular enzyme, is released outside the cell when the cell is damaged and detected in the medium. LDH was measured in accordance with the manufacturer's manual using Cytotoxicity LDH Assay Kit-WST (DOJINDO LABORATORIES).

In the Example, the amount of LDH released in the medium when the cells are damaged, relative to the amount of LDH contained in the whole cells, was examined and the ratio calculated was regarded as cytotoxicity.

$$\text{Cytotoxicity}(\%) = \frac{ER - ESR - TSR}{TMR - TSR} \times 100 \quad \text{[Expression 1]}$$

$$ER: OD^{ER}_{value} - OD^{CMB}_{value}$$

$$ESR: OD^{ESR}_{value} - OD^{CMB}_{value}$$

$$TSR: OD^{TSR}_{value} - OD^{CMB}_{value}$$

$$TMR: OD^{TMR}_{value} - OD^{VCC}_{value}$$

In the above expression, the experimental release (ER) represents the amount of LDF after mixing antibody solutions with each different concentration, effector cells, and target cells;

the spontaneous release (ESR) by the effector cells represents the amount of LDH spontaneously released from the effector cells, the target spontaneous release (TSR) represents the amount of LDH spontaneously released from the target cells;

the target maximum release (TMR) represents the whole LDH amount contained in the target cells and obtained by completely lysing the cells with a lysis buffer;

the culture medium background (CMB) represents the amount of LDH contained as a background in the medium; and volume correction control (VCC) represents the amount of LDH when the lysis buffer was added in the medium.

Figure 14:
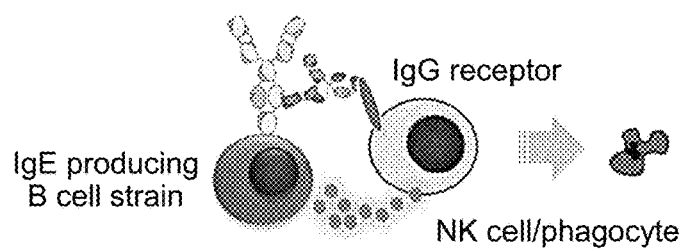
FIG. 14 shows cytotoxicity of 6C12 antibody to matured IgE antibody-producing B cells.

The results were as shown in FIG. 14. As shown in FIG. 14, the 6C12 antibody effectively killed the canine IgE-producing B cells.

Further, cytotoxicity of 6C12 antibody to IgE-producing B cells was examined in vitro. Human peripheral blood mononuclear cells were stimulated with an anti-CD40 antibody and recombinant IL-4 to induce an IgE-producing B cells. At this time, 6C12 or mouse IgG-containing mouse serum (negative control) was added and culture was carried out in 10% FBS-containing RPMI-1620 at 37° C. under 5% CO$_2$ for 5 days. The number of IgE-producing B cells that emerged in the medium was counted by ELISPOT method.

To wells of a PVDF membrane plate to which an anti-human IgE monoclonal antibody was immobilized, the cultured cells were added at a density of 8.4×10$^4$ cells/well, allowed to react for 24 hours and washed. Thereafter, a biotin labeled anti-human IgE monoclonal antibody and streptavidin-bound alkaline phosphatase were added, and then, a substrate was allowed to react to obtain color spots of IgE-producing B cells. The number of color spots that can be recognized by the naked eye, was counted.

Three wells per condition were subjected to assay. The cell counts were averaged and evaluated. The results were as shown in Table 4.
[Table 4]

TABLE 4

TABLE 4: Reduction of IgE producing cells

|  | Well 1 | Well 2 | Well 3 | Average |
|---|---|---|---|---|
| 6C12 300 μg/Well | 6 | 7 | 5 | 6 |
| Mouse IgG (serum 10%) | 38 | 26 | 35 | 33 |

In the wells to which 6C12 was added, 5 to 7 spots per well were counted (average 6 spots/well); whereas negative control wells to which mouse serum was added, 26 to 38 spots per well (average 33 spots/well) were counted. From this, it was found that 6012 has a suppressive action on production of IgE producing cells from human peripheral blood mononuclear cells. This was considered that 6C12 may directly act on IgE producing cells and cause cellular damage.

Example 8A: Decomposition of Sugar Chain on IgE by Enzyme Hydrolyzing Sugar Chain and Affinity of 6C12 Antibody for IgE In the Example, IgE antibody (Der f 2-IgE) to a mite allergen, Der f 2, was treated with PNGaseF, EndoH or neuraminidase to decompose a sugar chain thereof. Affinity of 6C12 antibody to Der f 2-IgE whose sugar chain was decomposed was confirmed.

The same test was carried out as in Example 3 except the enzyme treatment step. More specifically, recombinant-type Der f 2 (1 μg/mL in concentration) was added to a 96-well ELISA plate in a ratio of 100 ML/well and then immobilized at 4° C. overnight. After washing, 2% Gelatin-Biotin (0.1 μg/mL)-containing PBS (200 μL/well) was added. Blocking was made at room temperature for 2 hours and washing was carried out. As canine serum, serum samples taken from Der f 2-IgE-positive atopic dog and Der f 2 experimentally sensitized dog, were respectively used. The serum samples were previously subjected to Der f 2-IgE ELISA using heated/non-heated serum. The serum samples in which pathogenic IgE alone and non-pathogenic IgE alone were detected were respectively selected and put in use. These serum samples were diluted 200 fold, added in a ratio of 100 μL/well and allowed to stand still at room temperature for 6 hours. After washing, peptide-N-glycosidase F (PNGase F PRIME™, N-Zyme Scientifics) having a concentration of 250 units/mL and neuraminidase (α2-3,6,8 Neuramidase, New England BioLabs, Japan) having a concentration 100 units/mL were added in a ratio of 100 μL/well. After adding, incubation was carried out at 37° C. overnight. After washing, biotin-labeled 6C12 antibody (0.75 μg/mL) was added in a ratio of 100 μL/well and incubation was carried out at room temperature for 2 hours. After washing, streptavidin labeled β-galactosidase (Streptavidin-β-Gal conjugate, Sigma-Aldrich) having a concentration of 0.05 U/mL was added in a ratio of 100 ML/well and a reaction was carried out at room temperature for 2 hours. After washing, 0.1 mM 4-methylumbelliferyl β-D-galactopyranoside was added in a ratio of 100 μL/well and a reaction was carried out at room temperature for one hour. The β-galactosidase reaction was terminated by adding 0.25 M $Na_2CO_3$ in a ratio of 100 L/well. The fluorescent intensity of a decomposition product of the above substrate was measured in the conditions: an excitation wavelength of 355 mn, a fluorescence wavelength of 460 nm and cut off: 455 nm, by a fluorescent plate reader. Comparison was made to a standard canine serum whose Der f 2-IgE concentration was known.

Figure 19:
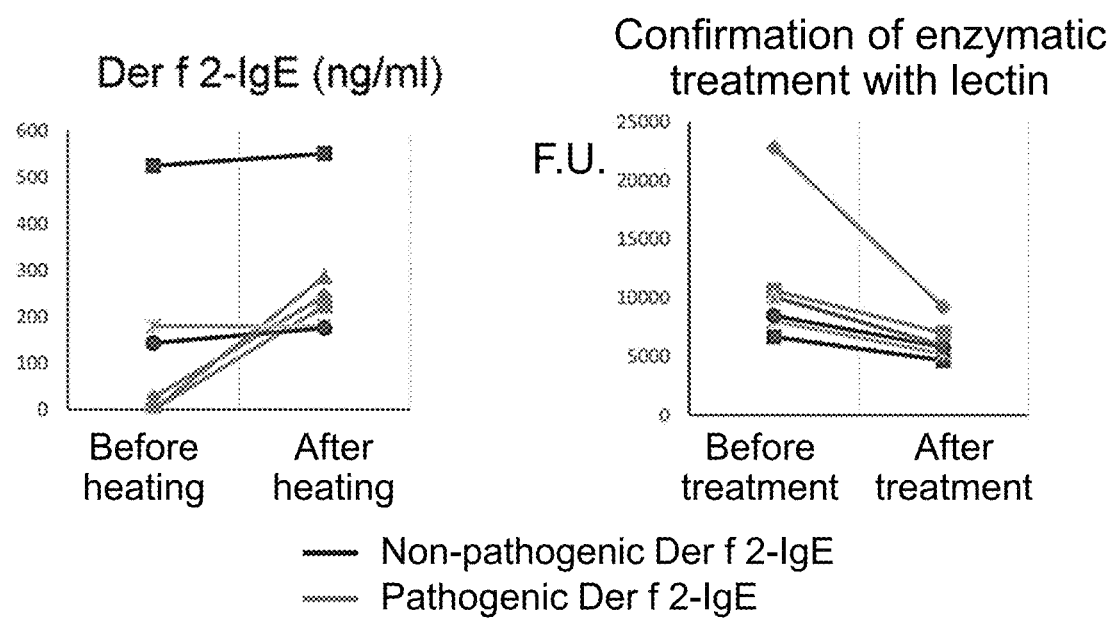
FIG. 19 shows that the binding property of 6C12 antibody to pathogenic IgE antibody varies depending on heating and shows the results of deglycosylation of pathogenic IgE antibody with α-2,3 neuraminidase.
Figure 24:
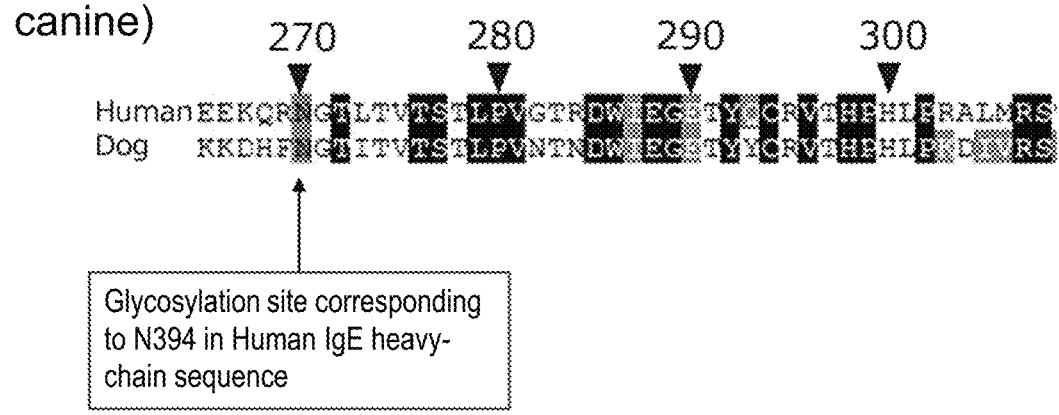
FIG. 24 shows the sequences of designated sites of IgE antibodies of a human and a dog in comparison.

The results were as shown in FIGS. 15 and 16 (PNGaseF treatment), FIGS. 17 and 18 (EndoH treatment) and FIGS. 19 and 20 (neuraminidase treatment).

As shown in FIGS. 15, 17 and 19, 6C12 antibody bound to pathogenic Der f 2-IgE in a heat treatment-dependent manner. When treated with an enzyme, pathogenic Der f 2-IgE lost binding property thereof to lectin (sugar-chain binding protein) as shown in FIGS. 15, 17 and 19. From this, it was found that a sugar chain was decomposed.

Herein, whether 6C12 antibody binds to non-pathogenic Der f 2-IgE and pathogenic Der f 2-IgE treated with an enzyme was confirmed. As a result, as shown in FIGS. 16 and 18, 6C12 antibody had affinity to pathogenic Der f 2-IgE treated with PNGaseF or EndoH. In contrast, as shown FIG. 20, 6C12 did not have affinity to pathogenic Der f 2-IgE treated with neuraminidase.

From these results, it was demonstrated that 6C12 antibody binds to pathogenic Der f 2-IgE antibody heated in an N-type glycosylation-dependent manner.

Example 9A: Identification of Epitope of 6C12 Antibody

It is considered that 6C12 antibody binds to a conserved region of a human and animals in a peptide sequence used as an immunogen, as shown in FIG. 25.

As shown in FIG. 21, Peptide (−3) and Peptide (−4) were prepared by deleting 3 amino acids and 4 amino acids respectively from the N terminal of a peptide sequence (Peptide-full) used as an immunogen. Peptide (−1C) to Peptide (−5C) were prepared by deleting 1 to 5 amino acids from the C terminal thereof. These peptides had 6×His tag followed by a glycine-serine linker (GS linker) at the N-terminal and were captured by an anti-His tag antibody. The binding to the biotinylated 6C12 antibody was detected with streptavidin-labeled β-galactosidase in accordance with a routine method. The results were as shown in FIG. 21. As shown in FIG. 21, Peptide (−3) alone maintained binding property to 6C12 antibody. Thus, it is considered that 6C12 antibody is an antibody recognizing Peptide (−3) as an epitope.

As shown in FIG. 22, the site of IgE antibody to which the 6C12 antibody is to be bound was simulated in silico and displayed. The site of the Peptide (−3) region is constituted of a helixes and B sheets and present in a protein surface. Peptide (−3) does not exist as a linear peptide. It is considered that 6C12 antibody can bind to the peptide portion since the conformation of the antibody is changed or the conformation of an epitope part is changed by heating pathogenic IgE or decomposing a sugar chain. Accordingly, it is considered that the antibody to be bound to Peptide (−3), since it selectively binds to heated pathogenic IgE and IgE on the surface of activated B cells similarly to 6C12 antibody, can be used for detecting pathogenic IgE and in targeting activated B cells.

Sequence Listing

SEQ ID NO: 1: Amino acid sequence of a canine peptide serving as an immunogen

SEQ ID NO: 2: Amino acid sequence of heavy chain CDR1 of 6C12 antibody

SEQ ID NO: 3: Amino acid sequence of heavy chain CDR2 of 6C12 antibody

SEQ ID NO: 4: Amino acid sequence of heavy chain CDR3 of 6C12 antibody
SEQ ID NO: 5: Amino acid sequence of light chain CDR1 of 6C12 antibody
SEQ ID NO: 6: Amino acid sequence of light chain CDR2 of 6C12 antibody
SEQ ID NO: 7: Amino acid sequence of light chain CDR3 of 6C12 antibody
SEQ ID NO: 8: Amino acid sequence of a heavy chain of 6C12 antibody
SEQ ID NO: 9: Amino acid sequence of a light chain of 6C12 antibody
SEQ ID NO: 10: Amino acid sequence of Peptide-full to which a 6×His tag and a GS linker sequence are bound
SEQ ID NO: 11: Amino acid sequence of Peptide (−3) to which a 6×His tag and a GS linker sequence are bound
SEQ ID NO: 12: Amino acid sequence of Peptide (−4) to which a 6×His tag and a GS linker sequence are bound
SEQ ID NO: 13: Amino acid sequence of Peptide (−3C) to which a 6×His tag and a GS linker sequence are bound
SEQ ID NO: 14: Amino acid sequence of Peptide (−4C) to which a 6×His tag and a GS linker sequence are bound
SEQ ID NO: 15: Amino acid sequence of Peptide (−5C) to which a 6×His tag and a GS linker sequence are bound
SEQ ID NO: 16: Amino acid sequence of Peptide (−2C) to which a 6×His tag and a GS linker sequence are bound
SEQ ID NO: 17: Amino acid sequence of Peptide (−1C) to which a 6×His tag and a GS linker sequence are bound
SEQ ID NO: 18: Amino acid sequence of Peptide (−3)

The invention claimed is:

1. An isolated monoclonal antibody or an antigen binding fragment thereof that binds to a peptide having an amino acid sequence of a heavy chain of IgE antibody corresponding to a sequence consisting of an amino acid sequence set forth in SEQ ID NO: 1 or 18,
   wherein the antibody and an antigen binding fragment thereof has
   a heavy chain variable region comprising heavy chain CDR1 having an amino acid sequence set forth in SEQ ID NO: 2, heavy chain CDR2 having an amino acid sequence set forth in SEQ ID NO: 3 and heavy chain CDR3 having an amino acid sequence set forth in SEQ ID NO: 4, and
   a light chain variable region comprising light chain CDR1 having an amino acid sequence set forth in SEQ ID NO: 5, light chain CDR2 having an amino acid sequence set forth in SEQ ID NO: 6 and light chain CDR3 having an amino acid sequence set forth in SEQ ID NO: 7.

2. The antibody or an antigen binding fragment thereof according to claim 1, wherein the antibody or an antigen binding fragment thereof has a heavy chain variable region having an amino acid sequence set forth in SEQ ID NO: 8, and a light chain variable region having an amino acid sequence set forth in SEQ ID NO: 9.

3. The antibody or an antigen binding fragment thereof according to claim 1, wherein the antibody or an antigen binding fragment thereof is caninized.

4. The antibody or an antigen binding fragment thereof according to claim 1, wherein the antibody or an antigen binding fragment thereof is felinized.

5. A pharmaceutical composition comprising the antibody or an antigen binding fragment thereof according to claim 1.

6. A composition comprising the antibody or an antigen binding fragment thereof according to claim 1, for use in detection of a free IgE antibody heated.

7. A method for examining an allergic symptom or a risk of developing the symptom in a mammal, comprising
   heating a biological sample obtained from a mammal to obtain a biological sample containing a free IgE antibody that reacts with the antibody according to claim 1, and
   bringing the heated biological sample into contact with the antibody or an antigen binding fragment thereof according to claim 1.

8. The method according to claim 7, further comprising bringing the biological sample of a mammal before heating into contact with the antibody or an antigen binding fragment thereof.

9. The method according to claim 8, further comprising comparing reactivity of the antibody or an antigen binding fragment thereof to a biological sample obtained from a mammal before and after heating the biological sample.

10. The antibody or an antigen binding fragment thereof according to claim 1, wherein the antibody or an antigen binding fragment thereof has a stronger affinity to an IgE antibody on the B cell surface than an IgE antibody on a mast-cell surface.

11. The antibody or an antigen binding fragment thereof according to claim 1, wherein the antibody or an antigen binding fragment thereof has a stronger affinity to a free IgE antibody heated at 56° C. than the free IgE antibody before heating.

12. A composition comprising the antibody or an antigen binding fragment thereof according to claim 2, for use in detection of a free IgE antibody heated.

13. A method for examining an allergic symptom or a risk of developing the symptom in a mammal, comprising
- heating a biological sample obtained from a mammal to obtain a biological sample containing a free IgE antibody that reacts with the antibody according to claim 2, and
- bringing the heated biological sample into contact with the antibody or an antigen binding fragment thereof according to claim 2.

14. The method according to claim 13, further comprising bringing the biological sample of a mammal before heating into contact with the antibody or an antigen binding fragment thereof.

15. The method according to claim 14, further comprising comparing reactivity of the antibody or an antigen binding fragment thereof to a biological sample obtained from a mammal before and after heating the biological sample.

\* \* \* \* \*

UNITED STATES PATENT AND TRADEMARK OFFICE
CERTIFICATE OF CORRECTION

| | | |
|---|---|---|
| PATENT NO. | : 12,319,751 B2 | Page 1 of 1 |
| APPLICATION NO. | : 17/278164 | |
| DATED | : June 3, 2025 | |
| INVENTOR(S) | : Masuda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this
Sixteenth Day of December, 2025

John A. Squires
*Director of the United States Patent and Trademark Office*

```
                           SEQUENCE LISTING

<160> NUMBER OF SEQ ID NOS: 18

<210> SEQ ID NO 1
   <211> LENGTH: 13
   <212> TYPE: PRT
   <213> ORGANISM: Artificial Sequence
   <220> FEATURE:
   <223> OTHER INFORMATION: Immunogen peptide

<400> SEQUENCE: 1

Asn Thr Asn Asp Trp Ile Glu Gly Glu Thr Tyr Tyr Cys
   1               5                   10

<210> SEQ ID NO 2
   <211> LENGTH: 10
   <212> TYPE: PRT
   <213> ORGANISM: Artificial Sequence
   <220> FEATURE:
   <223> OTHER INFORMATION: HCDR1

<400> SEQUENCE: 2

Gly Phe Asn Phe Asn Ala Tyr Val Met Asn
   1               5                   10

<210> SEQ ID NO 3
   <211> LENGTH: 22
   <212> TYPE: PRT
   <213> ORGANISM: Artificial Sequence
   <220> FEATURE:
   <223> OTHER INFORMATION: HCDR2

<400> SEQUENCE: 3

Trp Val Ser Arg Ile Arg Ser Lys Ser Asn Asn Tyr Ala Thr Tyr Tyr
   1               5                   10                  15

Ala Asp Ser Val Lys Asp
               20

<210> SEQ ID NO 4
   <211> LENGTH: 13
   <212> TYPE: PRT
   <213> ORGANISM: Artificial Sequence
   <220> FEATURE:
   <223> OTHER INFORMATION: HCDR3

<400> SEQUENCE: 4

Val Arg Pro Asp Tyr Tyr Gly Gly Ser Pro Phe Ala Tyr
   1               5                   10

<210> SEQ ID NO 5
   <211> LENGTH: 12
```

```
<212> TYPE: PRT
<213> ORGANISM: Artificial Sequence
<220> FEATURE:
<223> OTHER INFORMATION: LCDR1

<400> SEQUENCE: 5

Ser Ala Ser Ser Ser Val Ser Tyr Met Tyr Trp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: LCDR2

<400> SEQUENCE: 6

Pro Trp Ile Tyr Arg Thr Ser Asn Leu Ala Ser
1               5                   10

<210> SEQ ID NO 7
<211> LENGTH: 9
<212> TYPE: PRT
<213> ORGANISM: Artificial Sequence
<220> FEATURE:
<223> OTHER INFORMATION: LCDR3

<400> SEQUENCE: 7

Gln Gln Tyr His Ser Tyr Pro Pro Thr
1               5

<210> SEQ ID NO 8
<211> LENGTH: 212
<212> TYPE: PRT
<213> ORGANISM: Artificial Sequence
<220> FEATURE:
<223> OTHER INFORMATION: Variable Heavy Chain of 6C12

<400> SEQUENCE: 8

Asn Thr Thr His Tyr Arg Ala Ser Ser Gly Ile Asn Ala Glu Tyr Met
1               5                   10                  15

Gly Arg Gln Arg Thr Leu Ala Leu Ser Ser Phe Leu Val Phe Ser Thr
            20                  25                  30

Asp Asn Met Thr Leu Asn Met Leu Leu Gly Leu Lys Trp Val Phe Phe
        35                  40                  45

Val Val Phe Tyr Gln Gly Val His Cys Glu Val Gln Leu Val Glu Ser
    50                  55                  60

Gly Gly Gly Leu Val Gln Pro Lys Gly Ser Leu Lys Leu Ser Cys Ala
65                  70                  75                  80

Ala Ser Gly Phe Asn Phe Asn Ala Tyr Val Met Asn Trp Val Arg Gln
                85                  90                  95

Ala Pro Gly Lys Gly Leu Glu Trp Val Ser Arg Ile Arg Ser Lys Ser
            100                 105                 110

Asn Asn Tyr Ala Thr Tyr Tyr Ala Asp Ser Val Lys Asp Arg Phe Thr
        115                 120                 125

Ile Ser Arg Asp Asp Ser Glu Ser Met Leu Tyr Leu Gln Met Asn Asn
    130                 135                 140

Leu Lys Thr Glu Asp Thr Ala Met Tyr Tyr Cys Val Arg Pro Asp Tyr
145                 150                 155                 160

Tyr Gly Gly Ser Pro Phe Ala Tyr Trp Gly Gln Gly Thr Leu Val Thr
                165                 170                 175
```

```
Val Ser Ala Ala Lys Thr Thr Pro Pro Ser Val Tyr Pro Leu Ala Pro
            180                 185                 190

Gly Ser Ala Ala Gln Thr Asn Ser Met Val Thr Leu Gly Cys Leu Val
            195                 200                 205

Lys Gly Tyr Phe
        210

<210> SEQ ID NO 9
<211> LENGTH: 174
<212> TYPE: PRT
<213> ORGANISM: Artificial Sequence
<220> FEATURE:
<223> OTHER INFORMATION: Variable Light Chain of 6C12

<400> SEQUENCE: 9

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Ser
        35                  40                  45

Ser Ser Val Ser Tyr Met Tyr Trp Tyr Gln Gln Lys Pro Gly Ser Ser
    50                  55                  60

Pro Lys Pro Trp Ile Tyr Arg Thr Ser Asn Leu Ala Ser Gly Val Pro
65                  70                  75                  80

Ala Arg Phe Gly Gly Ser Gly Ser Gly Thr Ser Tyr Ser Leu Thr Ile
                85                  90                  95

Ser Ser Met Glu Ala Glu Asp Ala Ala Thr Tyr Tyr Cys Gln Gln Tyr
            100                 105                 110

His Ser Tyr Pro Pro Thr Phe Gly Val Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser
                165                 170

<210> SEQ ID NO 10
<211> LENGTH: 25
<212> TYPE: PRT
<213> ORGANISM: Artificial Sequence
<220> FEATURE:
<223> OTHER INFORMATION: Peptide-full

<400> SEQUENCE: 10

His His His His His His Gly Gly Ser Gly Gly Ser Asn Thr Asn Asp
1               5                   10                  15

Trp Ile Glu Gly Glu Thr Tyr Tyr Cys
            20                  25

<210> SEQ ID NO 11
<211> LENGTH: 22
<212> TYPE: PRT
<213> ORGANISM: Artificial Sequence
<220> FEATURE:
<223> OTHER INFORMATION: Peptide(-3

<400> SEQUENCE: 11

His His His His His His Gly Gly Ser Gly Gly Ser Asp Trp Ile Glu
```

-continued

```
                1               5                  10                 15
Gly Glu Thr Tyr Tyr Cys
            20

<210> SEQ ID NO 12
<211> LENGTH: 21
<212> TYPE: PRT
<213> ORGANISM: Artificial Sequence
<220> FEATURE:
<223> OTHER INFORMATION: Peptide(-4)

<400> SEQUENCE: 12

His His His His His His Gly Gly Ser Gly Gly Ser Trp Ile Glu Gly
1               5                   10                  15

Glu Thr Tyr Tyr Cys
            20

<210> SEQ ID NO 13
<211> LENGTH: 22
<212> TYPE: PRT
<213> ORGANISM: Artificial Sequence
<220> FEATURE:
<223> OTHER INFORMATION: Peptide(-3C)

<400> SEQUENCE: 13

His His His His His His Gly Gly Ser Gly Gly Ser Asn Thr Asn Asp
1               5                   10                  15

Trp Ile Glu Gly Glu Thr
            20

<210> SEQ ID NO 14
<211> LENGTH: 21
<212> TYPE: PRT
<213> ORGANISM: Artificial Sequence
<220> FEATURE:
<223> OTHER INFORMATION: Peptide(-4C)

<400> SEQUENCE: 14

His His His His His His Gly Gly Ser Gly Gly Ser Asn Thr Asn Asp
1               5                   10                  15

Trp Ile Glu Gly Glu
            20

<210> SEQ ID NO 15
<211> LENGTH: 20
<212> TYPE: PRT
<213> ORGANISM: Artificial Sequence
<220> FEATURE:
<223> OTHER INFORMATION: Peptide(-5C)

<400> SEQUENCE: 15

His His His His His His Gly Gly Ser Gly Gly Ser Asn Thr Asn Asp
1               5                   10                  15

Trp Ile Glu Gly
            20

<210> SEQ ID NO 16
<211> LENGTH: 23
<212> TYPE: PRT
<213> ORGANISM: Artificial Sequence
<220> FEATURE:
<223> OTHER INFORMATION: Peptide(-2C)

<400> SEQUENCE: 16
```

```
His His His His His His Gly Gly Ser Gly Gly Ser Asn Thr Asn Asp
1               5                   10                  15

Trp Ile Glu Gly Glu Thr Tyr
            20

<210> SEQ ID NO 17
<211> LENGTH: 24
<212> TYPE: PRT
<213> ORGANISM: Artificial Sequence
<220> FEATURE:
<223> OTHER INFORMATION: Peptide(-1C)

<400> SEQUENCE: 17

His His His His His His Gly Gly Ser Gly Gly Ser Asn Thr Asn Asp
1               5                   10                  15

Trp Ile Glu Gly Glu Thr Tyr Tyr
            20

<210> SEQ ID NO 18
<211> LENGTH: 10
<212> TYPE: PRT
<213> ORGANISM: Artificial Sequence
<220> FEATURE:
<223> OTHER INFORMATION: Epitope peptide of 6C12 antibody

<400> SEQUENCE: 18

Asp Trp Ile Glu Gly Glu Thr Tyr Tyr Cys
1               5                   10
```